United States Patent
Park et al.

(10) Patent No.: US 8,226,767 B2
(45) Date of Patent: Jul. 24, 2012

(54) HYBRID BANDGAP ENGINEERING FOR SUPER-HETERO-EPITAXIAL SEMICONDUCTOR MATERIALS, AND PRODUCTS THEREOF

(75) Inventors: Yeonjoon Park, Yorktown, VA (US);
Sang H. Choi, Poquoson, VA (US);
Glen C. King, Yorktown, VA (US);
James R. Elliott, Yorktown, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 933 days.

(21) Appl. No.: 12/254,134

(22) Filed: Oct. 20, 2008

(65) Prior Publication Data
US 2009/0220047 A1  Sep. 3, 2009

Related U.S. Application Data

(60) Provisional application No. 60/980,881, filed on Oct. 18, 2007, provisional application No. 60/980,880, filed on Oct. 18, 2007, provisional application No. 60/980,878, filed on Oct. 18, 2007, provisional application No. 60/980,871, filed on Oct. 18, 2007, provisional application No. 60/980,870, filed on Oct. 18, 2007.

(51) Int. Cl.
*C30B 25/18* (2006.01)
(52) U.S. Cl. ............... 117/84; 117/88; 117/89; 117/90; 117/91; 117/92; 117/93; 117/94; 117/101; 117/102; 117/103; 117/104; 117/105; 117/106; 117/107; 117/108
(58) Field of Classification Search .......... 117/84, 117/88–94, 101–108, 9
See application file for complete search history.

(56) References Cited

U.S. PATENT DOCUMENTS

| | | | |
|---|---|---|---|
| 4,357,183 A | 11/1982 | Fan et al. | |
| 5,205,871 A | 4/1993 | Godbey et al. | |
| 5,394,826 A | 3/1995 | Ebe et al. | |
| 5,667,586 A | 9/1997 | Ek et al. | |
| 5,709,745 A | 1/1998 | Larkin et al. | |
| 5,759,898 A | 6/1998 | Ek et al. | |

(Continued)

OTHER PUBLICATIONS

A publication to K. Balakrishnan, et al. entitled "Structural analyses of MBE grown cubic and hexagonal GaN epilayers by X-ray diffraction," Bulletin of the Electrochemical Laboatory, vol. 60, No. 10, 11, pp. 531-540 (1998).*

(Continued)

*Primary Examiner* — Michael Kornakov
*Assistant Examiner* — Kenneth A Bratland, Jr.
(74) *Attorney, Agent, or Firm* — Thomas K. McBride, Jr.; Robin W. Edwards

(57) ABSTRACT

"Super-hetero-epitaxial" combinations comprise epitaxial growth of one material on a different material with different crystal structure. Compatible crystal structures may be identified using a "Tri-Unity" system. New bandgap engineering diagrams are provided for each class of combination, based on determination of hybrid lattice constants for the constituent materials in accordance with lattice-matching equations. Using known bandgap figures for previously tested materials, new materials with lattice constants that match desired substrates and have the desired bandgap properties may be formulated by reference to the diagrams and lattice matching equations. In one embodiment, this analysis makes it possible to formulate new super-hetero-epitaxial semiconductor systems, such as systems based on group IV alloys on c-plane LaF$_3$; group IV alloys on c-plane langasite; Group III-V alloys on c-plane langasite; and group II-VI alloys on c-plane sapphire.

3 Claims, 26 Drawing Sheets

U.S. PATENT DOCUMENTS

| | | | |
|---|---|---|---|
| 5,769,964 | A | 6/1998 | Charache et al. |
| 5,951,757 | A * | 9/1999 | Dubbelday et al. ........... 117/102 |
| 6,096,389 | A | 8/2000 | Kanai |
| 6,100,546 | A * | 8/2000 | Major et al. .................. 257/103 |
| 6,306,211 | B1 | 10/2001 | Takahashi et al. |
| 6,488,771 | B1 | 12/2002 | Powell et al. |
| 6,524,935 | B1 | 2/2003 | Canaperi et al. |
| 6,562,127 | B1 | 5/2003 | Kud et al. |
| 6,627,809 | B1 | 9/2003 | Koga et al. |
| 6,653,658 | B2 | 11/2003 | Burden |
| 6,784,074 | B2 | 8/2004 | Shchukin et al. |
| 6,787,793 | B2 | 9/2004 | Yoshida |
| 7,247,885 | B2 | 7/2007 | Rankin et al. |
| 7,341,883 | B2 * | 3/2008 | Park et al. ....................... 438/46 |
| 7,368,335 | B2 | 5/2008 | Asami et al. |
| 7,558,371 | B2 | 7/2009 | Park et al. |
| 7,769,135 | B2 | 8/2010 | Park et al. |
| 7,906,358 | B2 | 3/2011 | Park et al. |
| 8,044,294 | B2 | 10/2011 | Park et al. |
| 2004/0147079 | A1 | 7/2004 | Forbes et al. |
| 2004/0173790 | A1 | 9/2004 | Yeo et al. |
| 2004/0190681 | A1 | 9/2004 | Omote |
| 2004/0201022 | A1 | 10/2004 | Yamazaki et al. |
| 2004/0214407 | A1 | 10/2004 | Westhoff et al. |
| 2004/0221792 | A1 | 11/2004 | Forbes |
| 2006/0163612 | A1 | 7/2006 | Kouvetakis et al. |
| 2006/0211221 | A1 | 9/2006 | Mantl et al. |
| 2006/0270200 | A1 | 11/2006 | Shibata |
| 2007/0069195 | A1 | 3/2007 | Park et al. |
| 2007/0168130 | A1 | 7/2007 | Sherwood et al. |
| 2007/0222034 | A1 * | 9/2007 | Park et al. .................... 257/616 |
| 2008/0113186 | A1 | 5/2008 | Kouvetakis et al. |
| 2008/0257395 | A1 | 10/2008 | Jovanovic et al. |
| 2009/0206368 | A1 | 8/2009 | Park et al. |
| 2009/0206369 | A1 | 8/2009 | Dang et al. |
| 2009/0220047 | A1 | 9/2009 | Park et al. |

OTHER PUBLICATIONS

H. Wado, et al. "Epitaxial growth of SiGe on Al2O3 using Si2H6 gas and Ge solid source molecular beam epitaxy," Journal of Crystal Growth, vol. 169, pp. 457-62 (1996).*

T.P. Humphreys, et al., "Heteroepitaxial growth and characterization of GaAs on silicon-on sapphire and sapphire substrates", Appl. Phys. Lett., 1989, vol. 54, pp. 1687-1689.

Nakamura, T. Mukai T, M. Senoh, "High-Power GaN P-N Junction Blue-Light-Emitting Diodes", Japanese Journal of Applied Physics Part 2-Letters 30 (12a): L1998-L2001 Dec. 1, 1991.).

O. Ambacher, "Growth and Applications of Group III-nitrides", Journal of Physics D—Applied Physics 31 (20): 2653-2710 Oct. 21, 1998.).

Yeonjoon Park, Michael J, Cich, Rian Zhao, Petra Specht, Eicke R. Weber, Eric Stach, Shinji Nozaki, "Analysis of Twin Defects in GaAs(111)B Moelcular Beam Epitaxy Growth", Journal of Vacuum Science and Technology B 18 (3): 1566-1571 May-Jun. 2000.).

S. SANORPIM E. Takum, R. Katayama, H. Ichinose, K. Onabe, Y. Shiraki, "Characterization of MOVPE-grown GaN layers on GaAs (111)B with a a cubic-GaN (111) epitaxial intermediate layer", Physica Status Solidi B-Basic Research 240 (2) : 305-309 Nov. 2003.

Z. Liliental-Weber, H. Sohn, N. Newman, J. Washburn, "Electron Microscopy Characterization of GaN Films Grown by Molecular-beam Epitaxy on Sapphire and SiC", Journal of Vacuum Science and Technology B 13 (4): 1578-1581-Jul.- Aug. 1995.

Y. Park. G.C. King, S. H. Choi, "Rhombohedral Epitaxy of Cubic SiGe on Trigonal c-plane sapphire", Journal of Crystal Growth 310 (2008) 2724-2731.

* cited by examiner

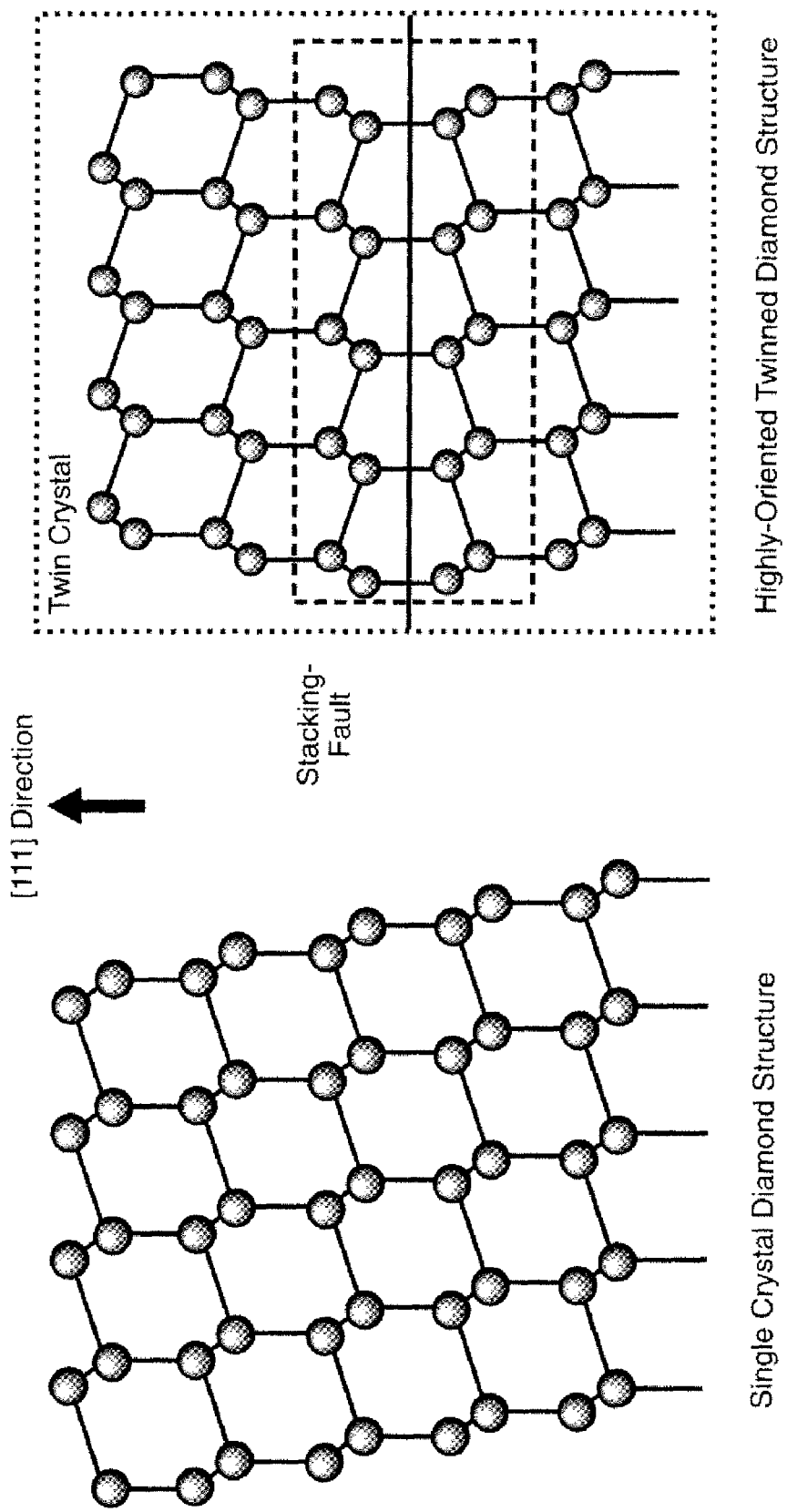

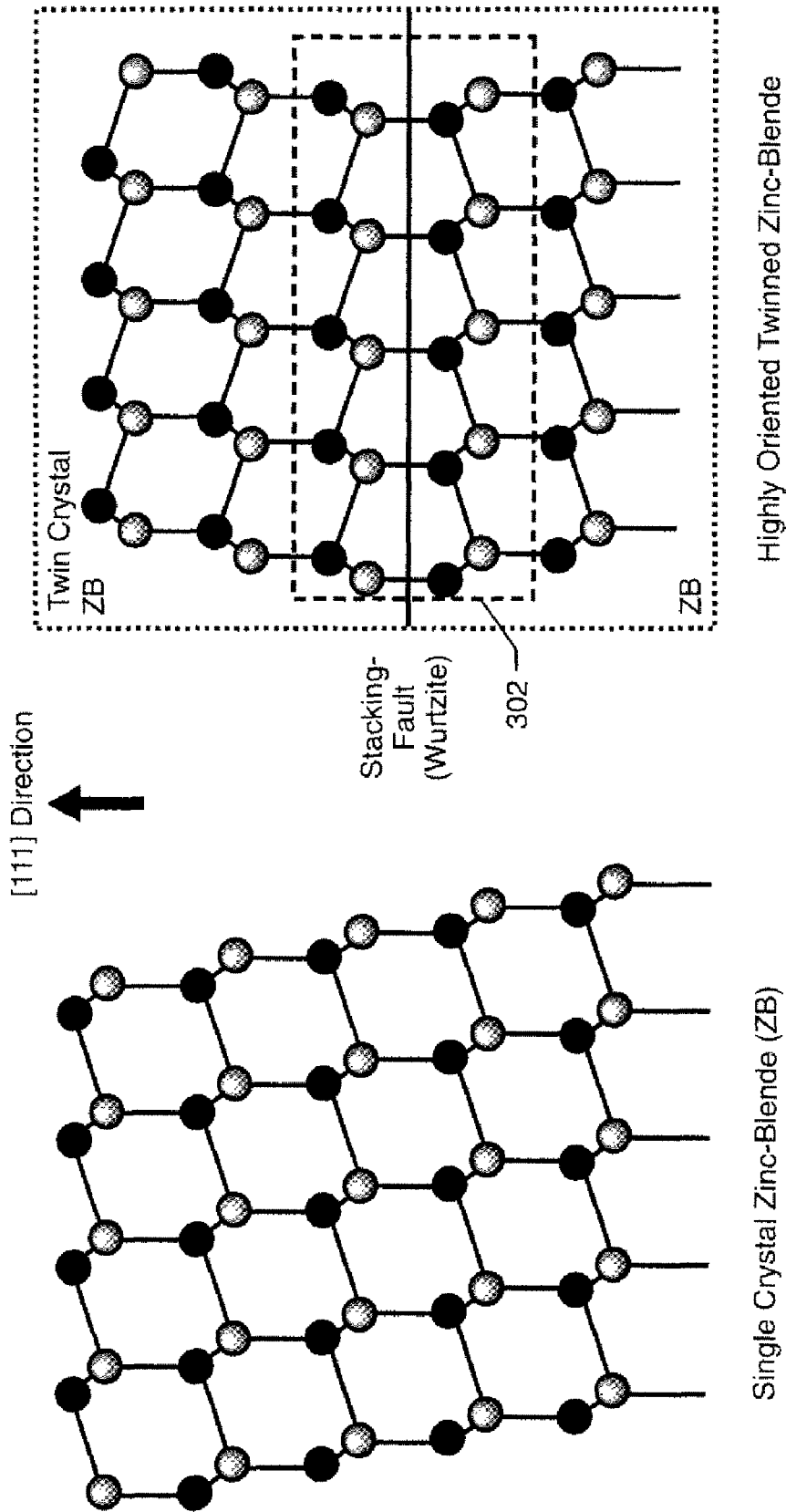

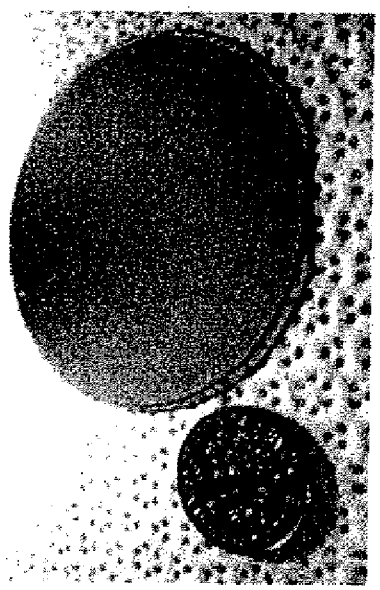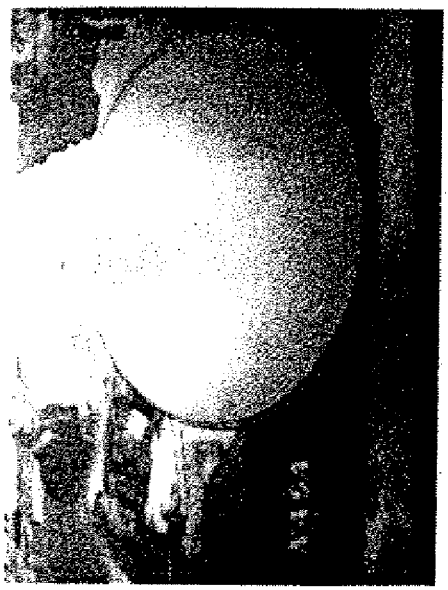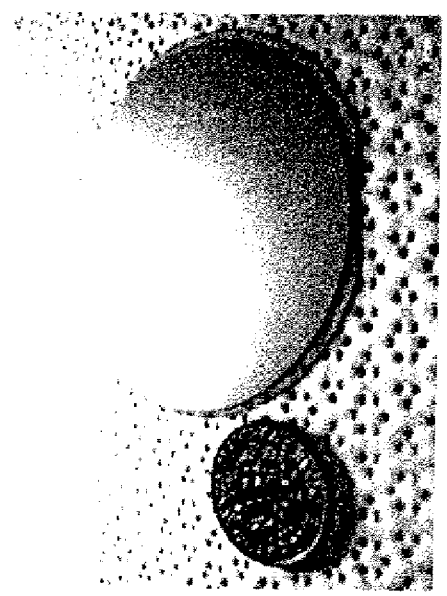
Fig. 13

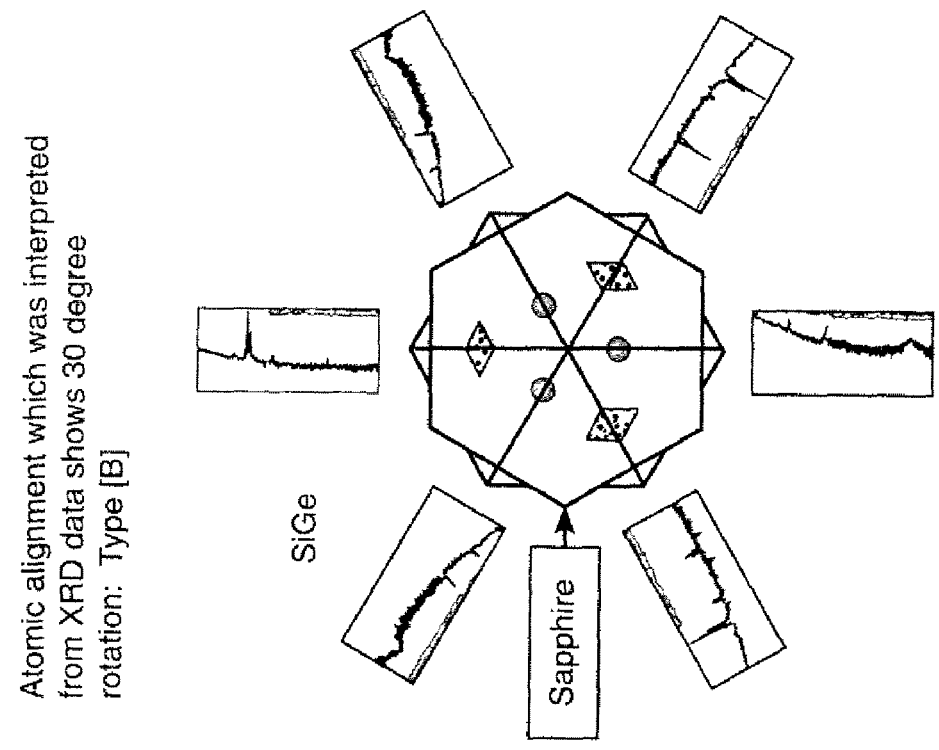
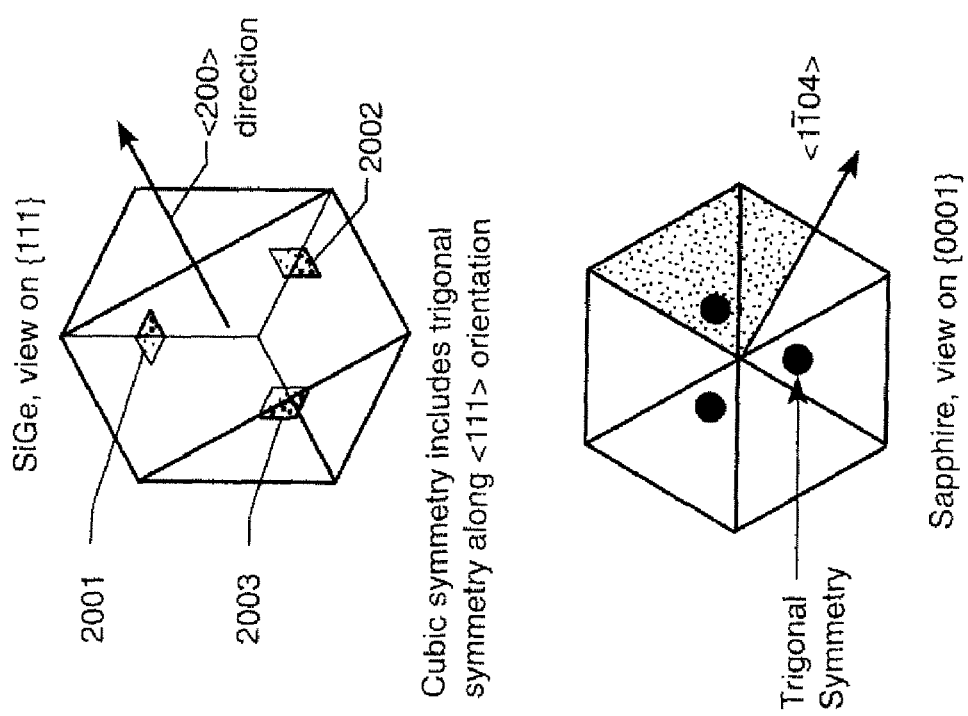
Fig. 20

HYBRID BANDGAP ENGINEERING FOR SUPER-HETERO-EPITAXIAL SEMICONDUCTOR MATERIALS, AND PRODUCTS THEREOF

ORIGIN OF THE INVENTION

This application claims the benefit of the respective filing dates of, and incorporates by reference the entire respective disclosures of, the following commonly assigned U.S. Provisional Patent Applications: Ser. No. 60/980,870 filed on Oct. 18, 2007, Ser. No. 60/980,871 filed on Oct. 18, 2007, Ser. No. 60/980,878 filed on Oct. 18, 2007, Ser. No. 60/980,880 filed on Oct. 18, 2007, and Ser. No. 60/980,881 filed on Oct. 18, 2007, each of which contains an overlap of inventive entity with the present application. In addition, this application incorporates by reference the entire disclosures of the following commonly assigned nonprovisional U.S. patent applications being filed on the same date as the present application: Ser. No. 12/254,017, now U.S. Pat. No. 7,906,358, entitled "EPITAXIAL GROWTH OF CUBIC CRYSTALLINE SEMICONDUCTOR ALLOYS ON BASAL PLANE OF TRIGONAL OR HEXAGONAL CRYSTAL;" Ser. No. 12/254,016, now U.S. Pat. No. 8,044,294, entitled "THERMOELECTRIC MATERIALS AND DEVICES;" Ser. No. 12/288,379, now U.S. Published Patent Application 2009/0206368, entitled "RHOMBOHEDRAL CUBIC SEMICONDUCTOR MATERIALS ON TRIGONAL SUBSTRATE WITH SINGLE CRYSTAL PROPERTIES AND DEVICES BASED ON SUCH MATERIALS;" Ser. No. 12/288,380, now U.S. Pat. No. 7,769,135, entitled "X-RAY DIFFRACTION WAFER MAPPING METHOD FOR RHOMBOHEDRAL SUPER-HETERO-EPITAXY;" and Ser. No. 12/254,150, now U.S. Pat. No. 7,558,371, entitled "METHOD OF GENERATING X-RAY DIFFRACTION DATA FOR INTEGRAL DETECTION OF TWIN DEFECTS IN SUPER-HETERO-EPITAXIAL MATERIALS;" each one claiming priority to the above-cited provisional applications.

CROSS-REFERENCE TO RELATED APPLICATIONS

This application claims the benefit of the respective filing dates of and incorporates by reference the entire respective disclosures of, the following commonly assigned U.S. Provisional Patent Applications: Ser. No. 60/980,870 filed on Oct. 18, 2007, Ser. No. 60/980,871 filed on Oct. 18, 2007, Ser. No. 60/980,878 filed on Oct. 18, 2007, Ser. No. 60/980,880 filed on Oct. 18, 2007, and Ser. No. 60/980,881 filed on Oct. 18, 2007, each of which contains an overlap of inventive entity with the present application. In addition, this application incorporates by reference the entire disclosures of the following commonly assigned nonprovisional U.S. patent applications being filed on the same date as the present application: Ser. No. 12/254,017, entitled "EPITAXIAL GROWTH OF CUBIC CRYSTALLINE SEMICONDUCTOR ALLOYS ON BASAL PLANE OF TRIGONAL OR HEXAGONAL CRYSTAL;" Ser. No. 12/254,016, entitled "THERMOELECTRIC MATERIALS AND DEVICES;" Ser. No. 12/288,379, entitled "RHOMBOHEDRAL CUBIC SEMICONDUCTOR MATERIALS ON TRIGONAL SUBSTRATE WITH SINGLE CRYSTAL PROPERTIES AND DEVICES BASED ON SUCH MATERIALS;" Ser. No. 12/288,380, entitled "X-RAY DIFFRACTION WAFER MAPPING METHOD FOR RHOMBOHEDRAL SUPER-HETERO-EPITAXY; " and Ser. No. 12/254,150, entitled "METHOD OF GENERATING X-RAY DIFFRACTION DATA FOR INTEGRAL DETECTION OF TWIN DEFECTS IN SUPER-HETERO-EPITAXIAL MATERIALS;" each one claiming priority to the above-cited provisional applications.

BACKGROUND OF THE INVENTION

1. Field of the Invention

The present invention is in the fields of solid-state physics and semiconductor materials, and more particularly concerns bandgap energy engineering analysis for new semiconductor alloy systems comprising hybrid epitaxial semiconductor crystal structures on heterogeneous substrates, including combinations of cubic, trigonal and hexagonal crystal materials.

2. Description of the Related Art

For the last 60 years since the invention of the first transistor by Bardeen, Brattain, and Shockley in 1947, the global microelectronics industry has used diamond structured group IV semiconductor crystals such as silicon (Si) and germanium (Ge). Another cubic compound semiconductor crystal structure, i.e. zinc-blende-alpha structure with group III-V and group II-VI, was also utilized by the semiconductor industry for the last 30 years. In the early 1990s, new semiconductor materials in different crystal structures were introduced in the microelectronics industry, including gallium nitride (GaN), aluminum nitride (AlN), and indium nitride (InN) in wurtzite structure. (See S. Nakamura, T. Mukai T, M. Senoh, Japanese Journal Of Applied Physics Part 2-Letters 30 (12a): L1998-L2001 Dec. 1, 1991.)

The term "bandgap" generally refers to the energy difference between the top of the valence hand and the bottom of the conduction band of a material, the energy gap that enables electrons to jump from one band to another. "Bandgap engineering" is the process of controlling or altering the bandgap of a material by controlling the composition of its constituent semiconductor alloys. Bandgap energy is a fundamental design parameter for semiconductor compositions, and has been particularly important in the design of heterojunction devices, as well as photoelectric devices such as laser diodes and solar cells.

The last 60 years of combined global effort in the field has resulted in a compilation of data showing bandgap energy as a function of the lattice constants associated with various semiconductor alloy compositions, for the diamond, zinc-blende and wurtzite structured materials referred to above. (See, e.g., V. Swaminathan, A. T. Macrander, Materials Aspects of GaAs and InP Based Structures, published by Prentice-Hall, p. 25 (1991); O. Ambacher, Journal of Physics D-Applied Physics 31 (20): 2653-2710 Oct. 21, 1998.)

The present work, including the other disclosures listed above which have been incorporated by reference herein, has involved development of new semiconductor materials with rhombohedral super-hetero epitaxial structures in various combinations of cubic, trigonal and hexagonal crystalline structures. The methods of determining lattice constants that underlie conventional bandgap engineering approaches translate directly to these new materials. Therefore, there was a need to develop a generalized engineering framework for relating these various crystal combinations, particularly in "super-hetero-epitaxial" combinations (i.e., epitaxial growth of one material on a different material with different crystal structure, and for specifying the bandgap energy engineering applicable to these classes of compositions.

SUMMARY OF THE INVENTION

It is an object of the present invention to develop relationships of bandgap energy as a function of lattice constants as applicable to super-hetero-epitaxial structures of cubic, trigonal and/or hexagonal crystalline materials, and corresponding methods of designing super-hetero-epitaxial semiconductor materials based thereon.

It is a further object of the invention to apply the foregoing techniques to formulate useful super-hetero-epitaxial semiconductor alloys in lattice-matched alignment.

Accordingly, the present invention, drawing on developments in lattice-matching, X-ray diffraction and wafer fabrication disclosed in related disclosures which have been incorporated herein by reference, is a "Tri-Unity" system by which compatible crystal structures may be identified, and provides new bandgap engineering diagrams for each class of combination based on the determination of hybrid lattice constants for the constituent materials in accordance with the lattice-matching equations.

Using known bandgap figures for previously tested materials, new materials with lattice constants that match desired substrates and have the desired bandgap properties may be formulated by reference to the diagrams and lattice matching equations.

In one embodiment, the foregoing analysis makes it possible to formulate new super-hetero-epitaxial semiconductor systems, such as systems based on group IV alloys on c-plane $LaF_3$; group IV alloys on c-plane langasite; Group III-V alloys on c-plane langasite; and group II-VI alloys on c-plane sapphire.

Other aspects and advantages of the invention will be apparent from the accompanying drawings, and the detailed description that follows.

BRIEF DESCRIPTION OF THE DRAWINGS

For a more complete understanding of the present invention and the advantages thereof, reference is now made to the following description taken in conjunction with the accompanying drawings, wherein like reference numerals represent like parts, in which:

FIG. 2 is a schematic illustration of (a) single crystal, and (b) twinned diamond structure (Si, Ge, and C) with stacking fault.

FIG. 3 is a schematic illustration of (a) single crystal, and (b) twinned zinc-blende structure (group III-V and group II-VI) with stacking fault.

FIG. 13 contains photographs of diamond structured SiGe semiconductor alloy layers grown on c-plane sapphire substrate with trigonal space symmetry.

FIG. 20 is a schematic illustration of the atomic alignment of majority (92% in above sample) single crystal SiGe on c-plane sapphire.

DETAILED DESCRIPTION

The following is a detailed description of certain embodiments of the invention chosen to provide illustrative examples of how it may preferably be implemented. The scope of the invention is not limited to the specific embodiments described, nor is it limited by any specific implementation, composition, embodiment or characterization depicted in the accompanying drawings or stated or described in the invention summary or the abstract. In addition, it should be noted that this disclosure describes a number of methods that each comprise a plurality of steps. Nothing contained in this written description should be understood to imply any necessary order of steps in such methods, other than as specified by express claim language.

In the ensuing description, the well-known Miller indices notation of lattice planes is used. That is, crystal planes are designated by numbers within "( )", groups of similar planes are designated by numbers within "{ }", direction or length is designated by numbers within "[ ]", and groups of similar directions are designated by numbers within "< >".

Figure 1B:
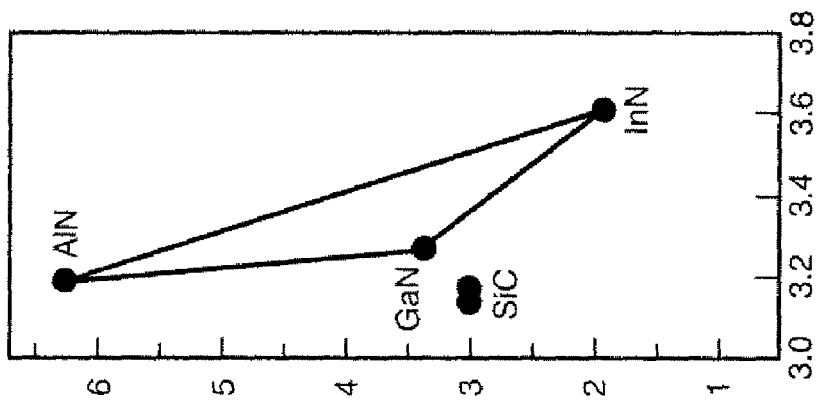
FIG. 1 shows graphs of results from prior studies showing (a) bandgap engineering with diamond (IV) and zinc-blende structures (III-V and II-VI), and (b) bandgap engineering with wurtzite hexagonal structures.
Figure 1A:
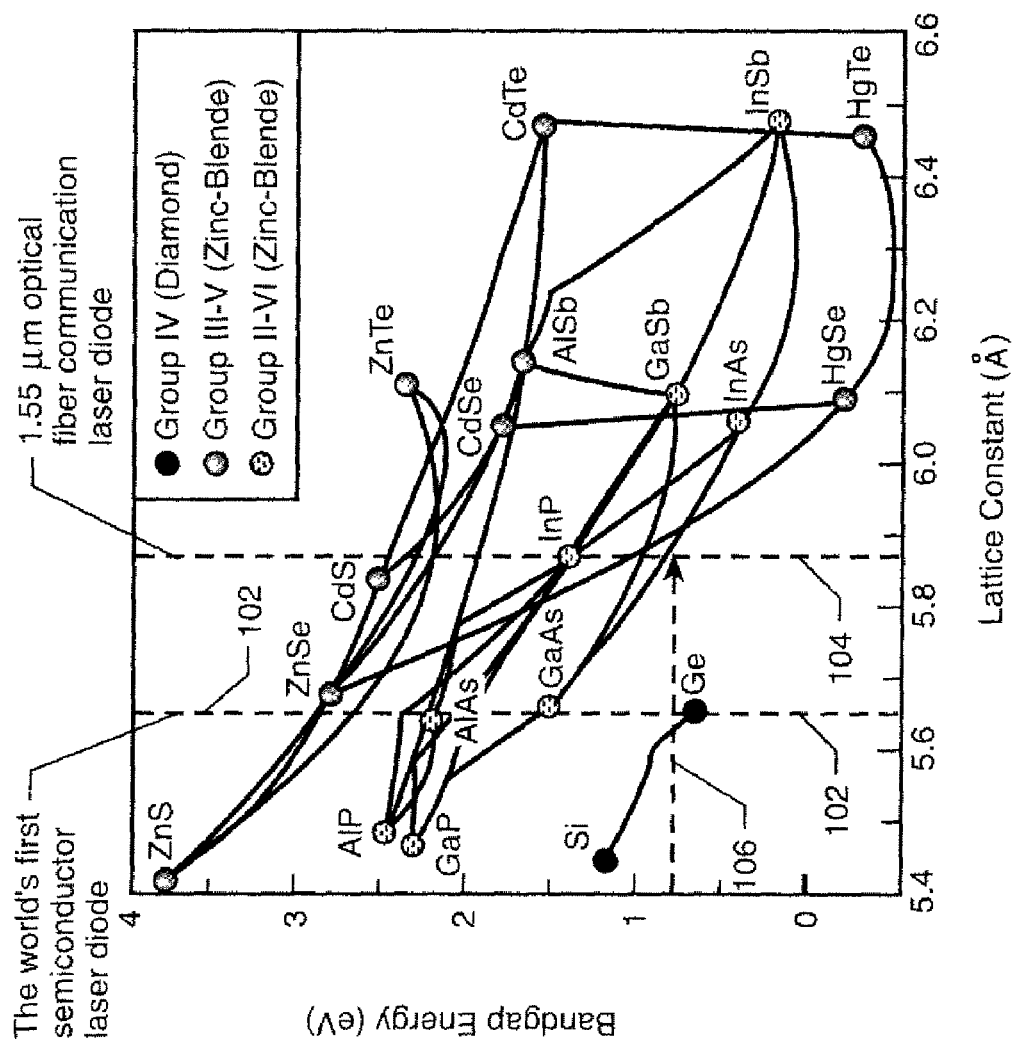

FIG. 1(a) is a bandgap engineering diagram reflecting a previously established and widely accepted mathematical diagram with group IV semiconductor materials in cubic diamond structure and group II-V and group II-VI materials in cubic zinc-blende structure. FIG. 1(b) is a similar diagram, but for semiconductor materials with wurtzite hexagonal crystal structures.

We refer to zinc-blende-alpha structure as zinc-blende (ZB) structure, which is a diatomic variation of diamond structure. Group III-V semiconductor includes gallium arsenide (GaAs), indium arsenide (InAs), aluminum arsenide (AlAs), gallium phosphide (GaP) and other combinations from these groups in the periodic table. Group II-VI semiconductor includes zinc selenide (ZnSe), zinc telluride (ZnTe), cadmium sulfide (CdS) and other combinations from those groups in the periodic table. The uniform alloys made with these groups have unique and different bandgap energy and different average-lattice-constants from the original materials, as shown in the connecting lines in FIG. 1(a). The averaged lattice constant of uniform pseudo alloy was very important to fabrication of defect-free semiconductor devices, while the bandgap energy of group III-V and II-VI materials determined the wavelength for emitting or absorbing light. For example, dotted line 102 shows that the world's first semiconductor laser diode was built with the almost-lattice-matched two semiconductor materials, GaAs and AlAs. As another example, dotted line 104 shows that the alloy of InGaAs can match the lattice constant (see line 106) of InP substrate and match the bandgap energy of 1.55 micrometer optical fiber communication wavelength. The most efficient and reliable fiber communication InGaAs laser diode was built on dotted line 104 in FIG. 1(a).

Additional semiconductor materials in wurtzite structure that were introduced in the early 1990s were gallium nitride (GaN), aluminum nitride (AlN), and indium nitride (InN). Because wurtzite structure has trigonal point symmetry and hexagonal space symmetry, it could not be merged with cubic III-V structure; instead, it formed a separate bandgap diagram as shown in FIG. 1(b).

The above two bandgap engineering diagrams were built by many researchers' efforts and it is the engineering summary of various semiconductor materials science for the last 60 years of global achievement.

An additional class of bandgap engineering diagrams, for rhombohedral super-hetero-epitaxy of three different crystal structures, cubic (diamond and zinc-blende), trigonal, and hexagonal crystals will now be established.

(1) X-Ray Characterization of Homo-Epitaxy

As further background, XRD methods for investigating stacking faults and twinning in homo-epitaxial structures have previously been published. (See Yeonjoon Park, Michael J. Cich, Rian Zhao, Petra Specht, Eicke R. Weber, Eric Stach, Shinji Nozaki, Journal of Vacuum Science & Technology B 18 (3): 1566-1571 May-June 2000.) FIGS. 2 and 3 show the twinned diamond structure and zinc-blende structure as a result of stacking fault in (111) plane. The X-ray characterization of twinning during homo-epitaxy growth on the (111) plane was successfully developed in the cited Park et al. publication. That publication noted that the stacking fault in ZB structure is the same as one monolayer of embedded wurtzite structure, as shown in dotted box 302 in FIG. 3(b). The idea of mixed crystal structures was further investigated by Sanorpim, Shiraki, and others with hexagonal (wurtzite) and later with cubic (zinc-blende) GaN epitaxy on GaAs (111). (See B. S. Sanorpim S, E. Takuma, R. Katayama, H. Ichinose, K. Onabe, Y. Shiraki, Physica Status Solidi B-Basic Research 240 (2): 305-309 November 2003.)

2) Development of Analysis for Super-Hetero-Epitaxy

Figure 4B:
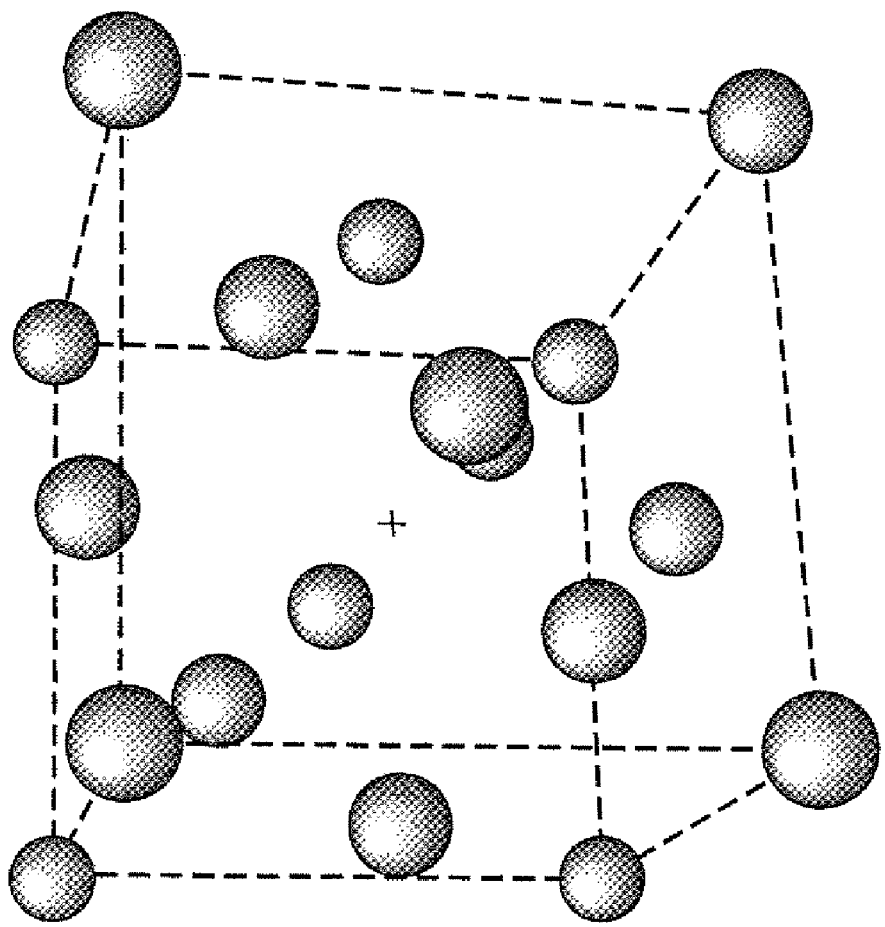
FIG. 4 illustrates perspective views showing crystal structure of unit cells: (a) sapphire (Al2O3), and (b) group IV alloy of Si, Ge, C, and Sn.
Figure 4A:
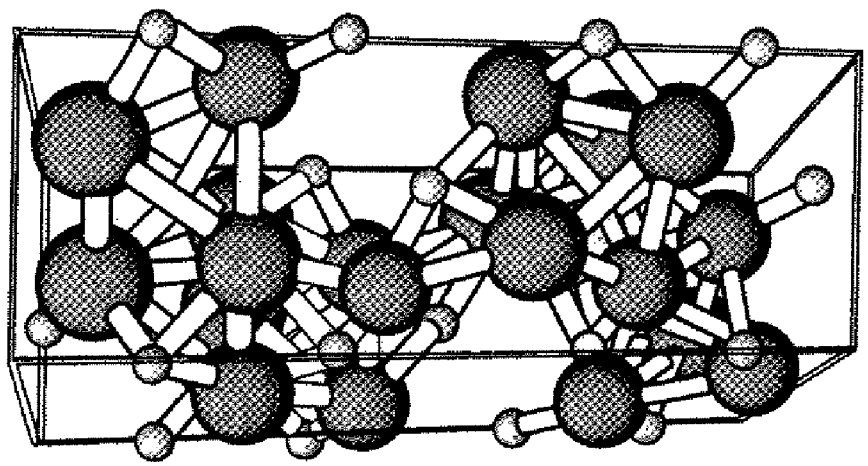

As developed in an accompanying disclosure that has been incorporated herein by reference (U.S. patent application Ser. No. 12/288,379, entitled "RHOMBOHEDRAL CUBIC SEMICONDUCTOR MATERIALS ON TRIGONAL SUBSTRATE WITH SINGLE CRYSTAL PROPERTIES AND DEVICES BASED ON SUCH MATERIALS"), which we shall herein refer to as the "CRYSTAL GROWTH disclosure", we have investigated the growth of diamond structured group IV alloys on basal plane of trigonal crystals such as c-plane sapphire. FIG. 4 shows the crystal structure of sapphire and diamond structure of group IV alloy made with Si, Ge, C, and Sn.

The primary purpose of the epitaxial trial was to align <111> direction of cubic diamond structure with <0001> direction of trigonal sapphire substrate. After trials, we found that there existed difficulties resulting from the trigonal symmetry of the <111> direction of cubic crystals. In many cases, the epitaxial layer showed two possible in-plane alignments, as shown in the top view in FIG. 5(b).

Figure 5B:
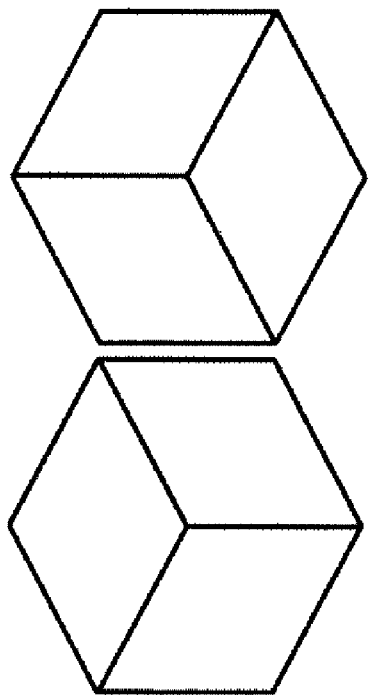
FIG. 5 show perspective views of (a) rhombohedral alignment: <111> direction of cubic crystal aligned with <0001> direction of trigonal substrate, and (b) two possible in-plane azimuthal alignments inside rhombohedral alignment.
Figure 5A:
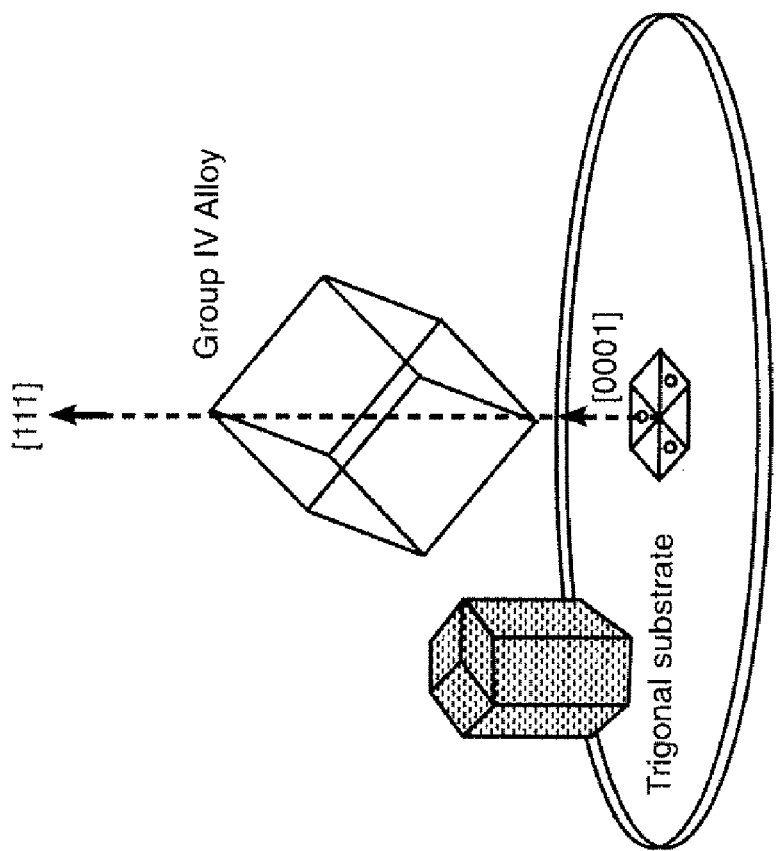

The two cubic crystals in FIG. 5(b) are twin crystals rotated by 60° in the {111} plane. High quality semiconductors require one single crystal structure all across the water. Therefore, if one cubic structure is a desired structure, the other structure becomes a twin (or "double position") defect. However, the origin and nature of this defect was very different from the homo-epitaxy case. In the case of homo-epitaxy of GaAs (111)B, the stacking fault occurs at any place inside epitaxial layer during the growth, but in the case of rhombohedral growth of group IV alloys on c-plane sapphire, the stacking fault can occur (1) at the interface and (2) inside the epitaxial layer. Therefore, the twin defect of rhombohedral epitaxy on trigonal substrate made for a very different case, unlike the previous homo-epitaxy study. We found that most of the twin defect came from the interfacial defects rather than internal stacking faults in the middle of epitaxial layer.

The term "Super-hetero-Epitaxy" is used herein to refer to the epitaxial growth of one material on a different material with different crystal structures in order to distinguish it from conventional hetero-epitaxy, growth on a different material with same crystal structure. We may consider the well-known epitaxial growth of GaN and AlN which have hexagonal space symmetry on c-plane sapphire which has trigonal space symmetry as one example of super-hetero epitaxy.

Figure 6B:
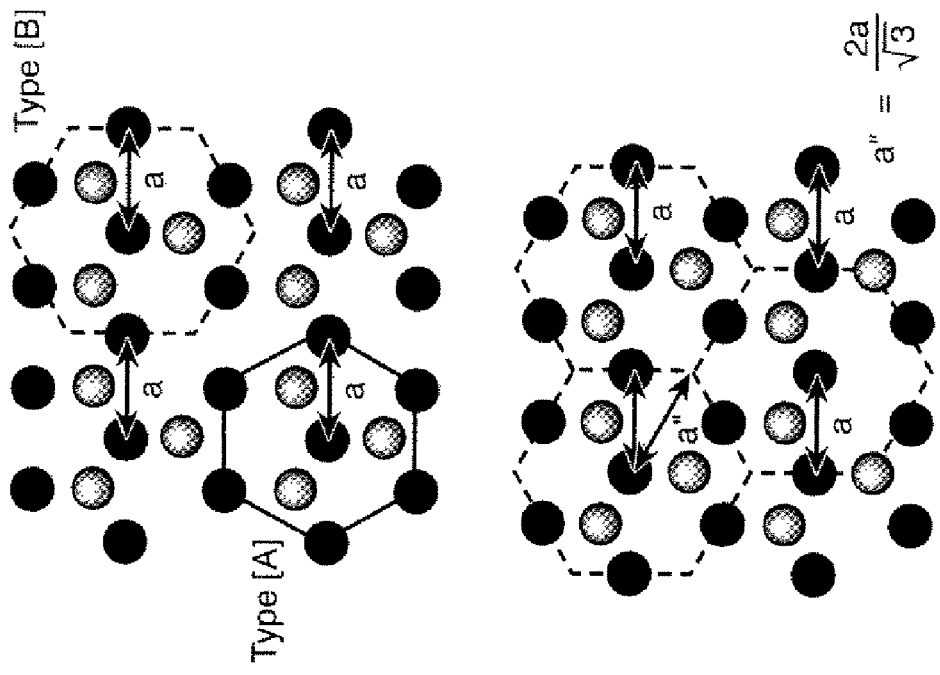
FIG. 6 is a schematic illustration showing (a) basal plane of simplified crystal structure of sapphire with trigonal space symmetry and {111} plane of diamond structure which has trigonal symmetry, (b) Type [A] (lower left) and Type [B] (upper right) atomic alignments; and (c) further detail of Type [B] alignment.
Figure 6A:
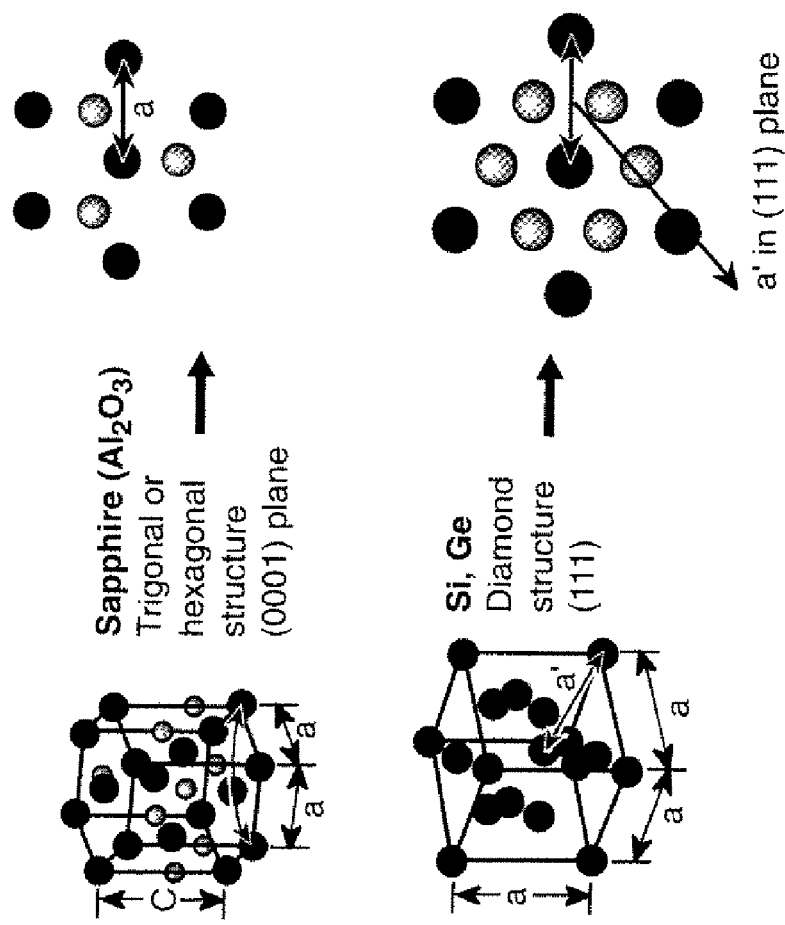
Figure 7:
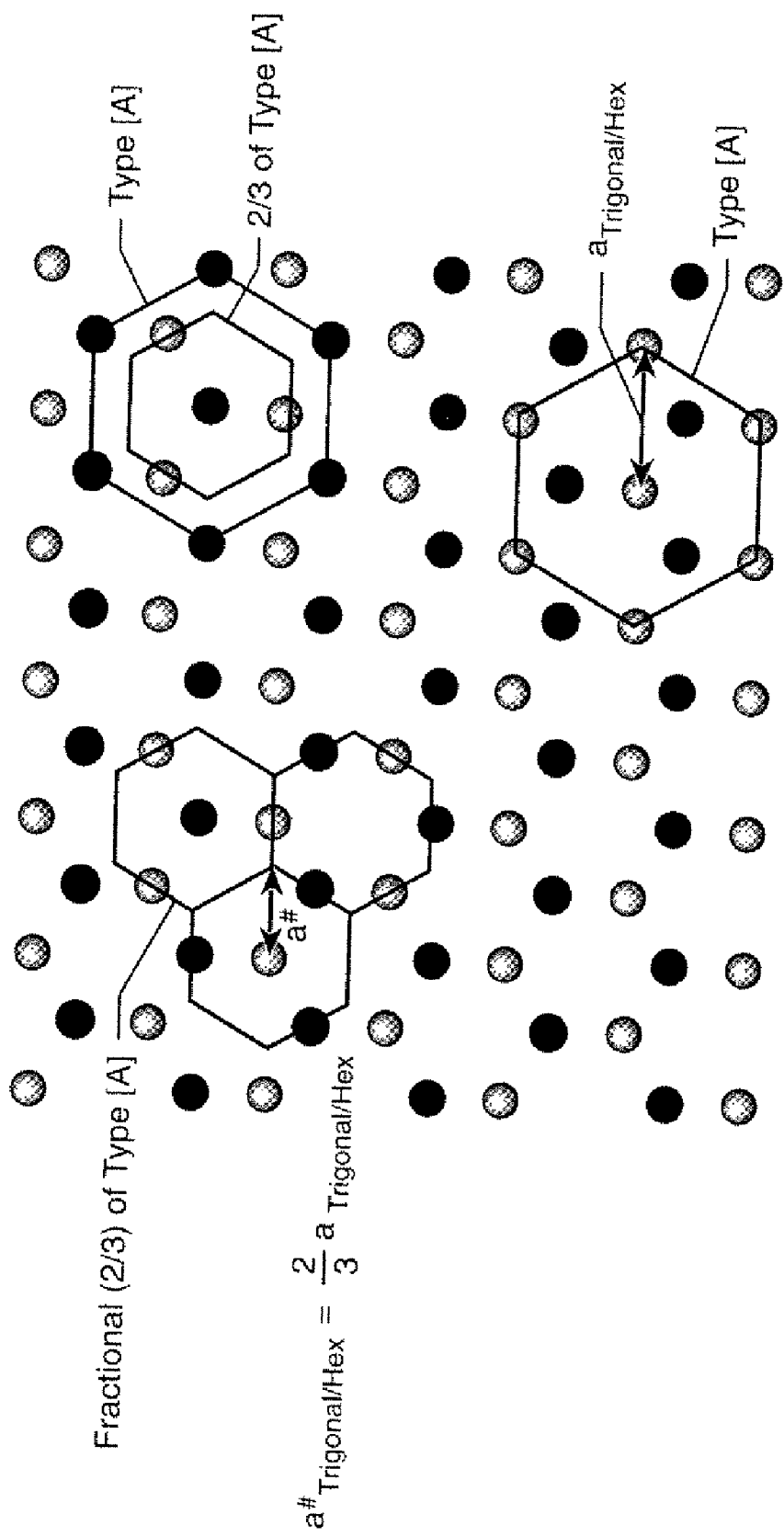
FIG. 7 is a schematic illustration showing fractional (⅔) of Type-A Alignment.
Figure 8:
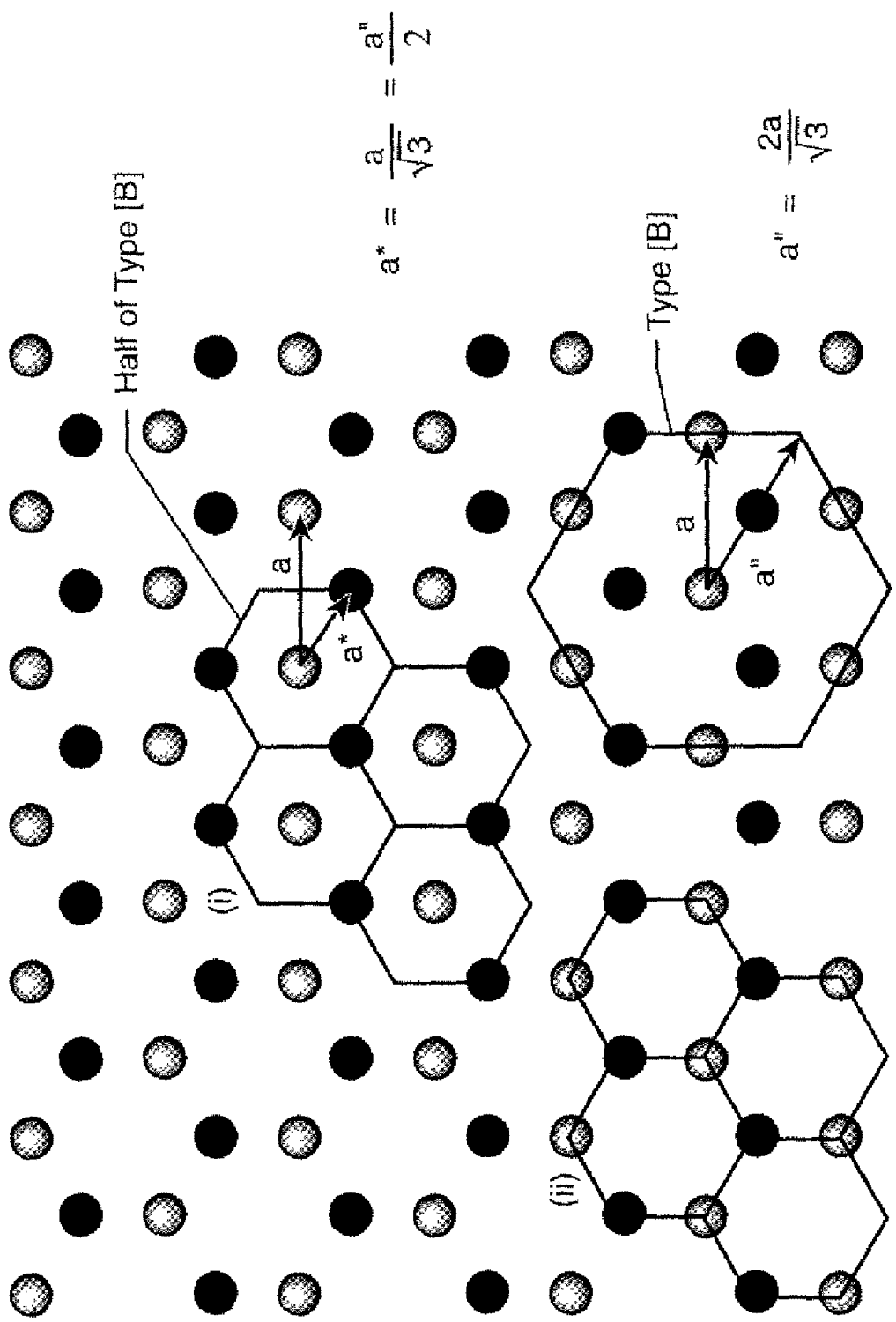
FIG. 8 is a schematic illustration showing "Half of Type [B]" atomic alignments (i) and (ii) at the interface between the {111} plane of cubic crystal and the basal plane of trigonal crystal.

In another disclosure which has been incorporated herein by reference (U.S. patent application Ser. No. 12/254,017, entitled "EPITAXIAL GROWTH OF GROUP IV CUBIC CRYSTALLINE SEMICONDUCTOR ALLOYS ON BASAL PLANE OF TRIGONAL OR HEXAGONAL CRYSTAL"), herein referred to as the "LATTICE MATCH- ING disclosure", the development of four lattice-matching equations for rhomohedrally aligned cubic crystals on trigonal substrates was represented in a hexagonal coordinate system. In that disclosure, four types of alignment were identified between the cubic and underlying trigonal systems, as shown in FIGS. 6, 7 and 8. These are Type [A] alignment and Type [B] alignment, as shown in FIG. 6(*b*) (bottom-left and top-right, respectively), and the "fractional alignments," ⅔ of Type [A] alignment (FIGS. 7), and ½ of Type [B] alignment (FIG. 8).

The atomic alignment of {111} plane of cubic diamond and zinc-blende structure is shown in FIG. 6 with respect to the basal plane of trigonal lattice of sapphire. In "Type [A]" alignment, the hexagonal ring of atomic sites of {111} plane of cubic crystal directly meets the hexagonal ring or atomic sites in trigonal basal plane without any rotations as shown in the lower-left of FIG. 6(*b*). In "Type [B]" alignment, the hexagonal ring of atomic sites of {111} plane of cubic crystal meets the hexagonal ring of atomic sites in trigonal basal plane with 30° rotation, as shown in the upper right of FIG. 6(*b*). In trigonal symmetry, 30° rotation is the same as 90° rotation.

In addition, there are two more lattice matching conditions with fractional alignment of Type [A] and Type [B], which are referred to as "⅔ of Type [A]" and "½ of Type [B]" alignments, as shown in FIGS. 7 and 8, respectively. Fractional "⅔ of Type [A]" alignment is shown in FIG. 7. Fractional "(½) of Type [B]" atomic alignments are shown in two sets as (i) and (ii) in FIG. 8.

The corresponding lattice-matching equations (for matching the cubic with the underlying trigonal structures in these four cases) are, respectively, as follows:

$$L_{target} = \frac{2}{\sqrt{3}} a_{Tri/Hex} \text{ for Type } [A] \text{ alignment} \quad (1)$$

$$L_{target} = \frac{4}{3} a_{Tri/Hex} \text{ for Type } [B] \text{ alignment} \quad (2)$$

$$L_{target} = \frac{4}{3\sqrt{3}} a_{Tri/Hex} \text{ for 2/3 of Type } [A] \text{ alignment} \quad (3)$$

$$L_{target} = \frac{2}{3} a_{Tri/Hex} \text{ for 1/2 of Type } [B] \text{ alignment} \quad (4)$$

In the related XRD disclosures, (1) integral XRD method ("METHOD OF GENERATING X-RAY DIFFRACTION DATA FOR INTEGRAL DETECTION OF TWIN DEFECTS IN SUPER-HETERO-EPITAXIAL MATERIALS") to measure average twin defect concentration with the development of three twin-defect detection X-Ray diffraction techniques and (2) XRD wafer mapping method ("X-RAY DIFFRACTION WAFER MAPPING METHOD FOR RHOMBOHEDRAL SUPER-HETERO-EPITAXY") using {440} peaks to locate twin defect position are used to verify the structure of the fabricated materials, and can also be adapted for nondestructive quality control and wafer selection.

Figure 9:
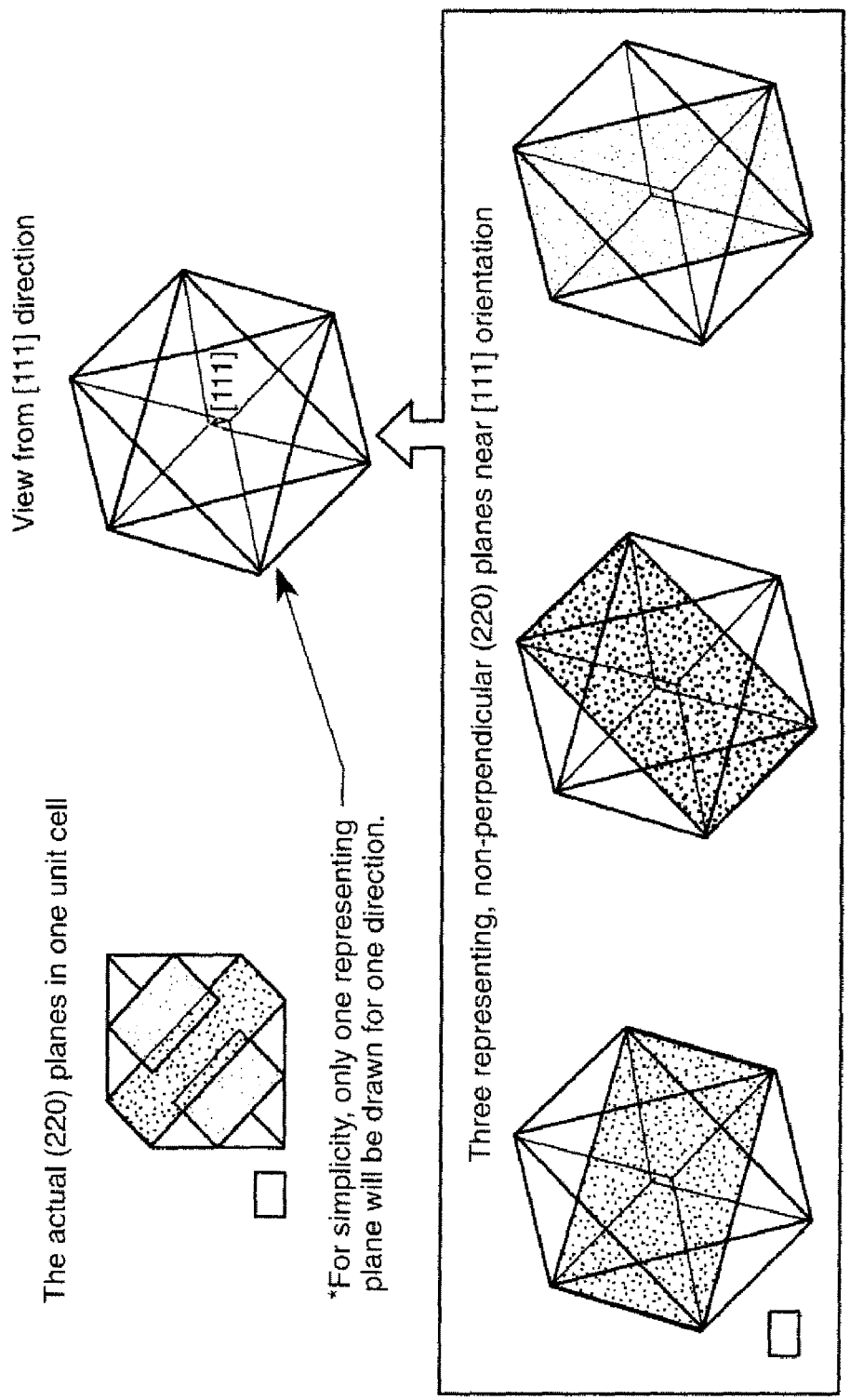
FIG. 9 shows perspective views of three similar planes with a rotation along the <111> axis of cubic crystal structure.

FIG. 9 shows three folded {220} planes of a cubic structure with a rotation along the <111> axis. For diamond structure and zinc-blende structure, {220} planes are a good choice for X-ray diffraction since they have strong diffraction intensity which can be calculated from the structure factor. Other three-folded planes along <111> axis, such as {004}, {113}, {224} and so on, can be used as well, although their X-ray diffraction intensity is not as good as those of the {220} planes. For other crystal structures, like Face Centered Cubic (FCC) materials, different planes can be considered with different structure factors.

Figure 10:
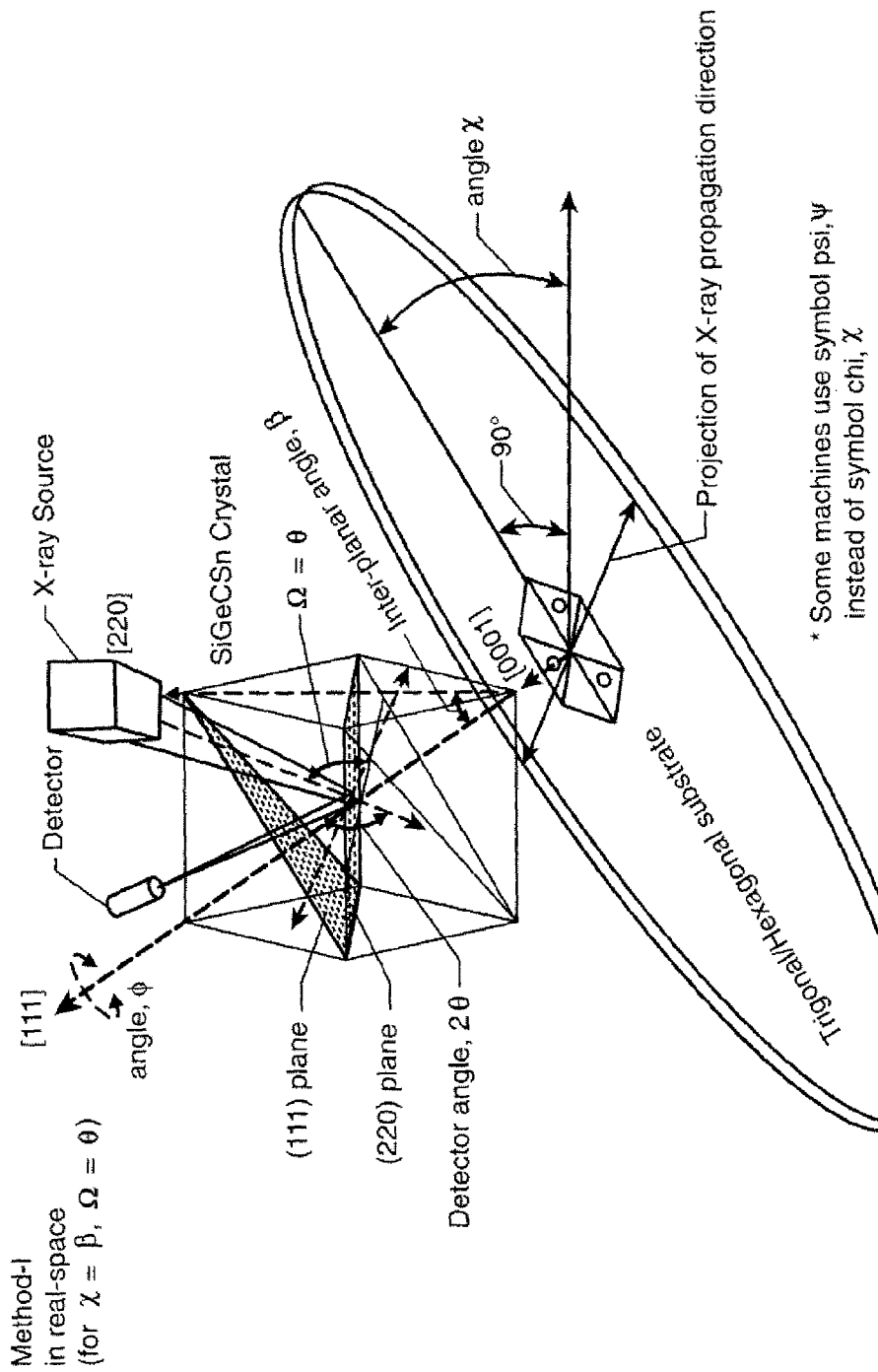
FIG. 10 is a schematic illustration showing the apparatus of X-ray diffraction method-1 of related disclosures, U.S. patent application Ser. No. 12/254,150, entitled "METHOD OF GENERATING X-RAY DIFFRACTION DATA FOR INTEGRAL DETECTION OF TWIN DEFECTS IN SUPER-HETERO-EPITAXIAL MATERIALS," and U.S. patent application Ser. No. 12/288,380, entitled "X-RAY DIFFRACTION WAFER MAPPING METHOD FOR RHOMBOHEDRAL SUPER-HETERO-EPITAXY," each incorporated herein by reference; both herein referred to as the "XRD disclosures."
Figure 11:
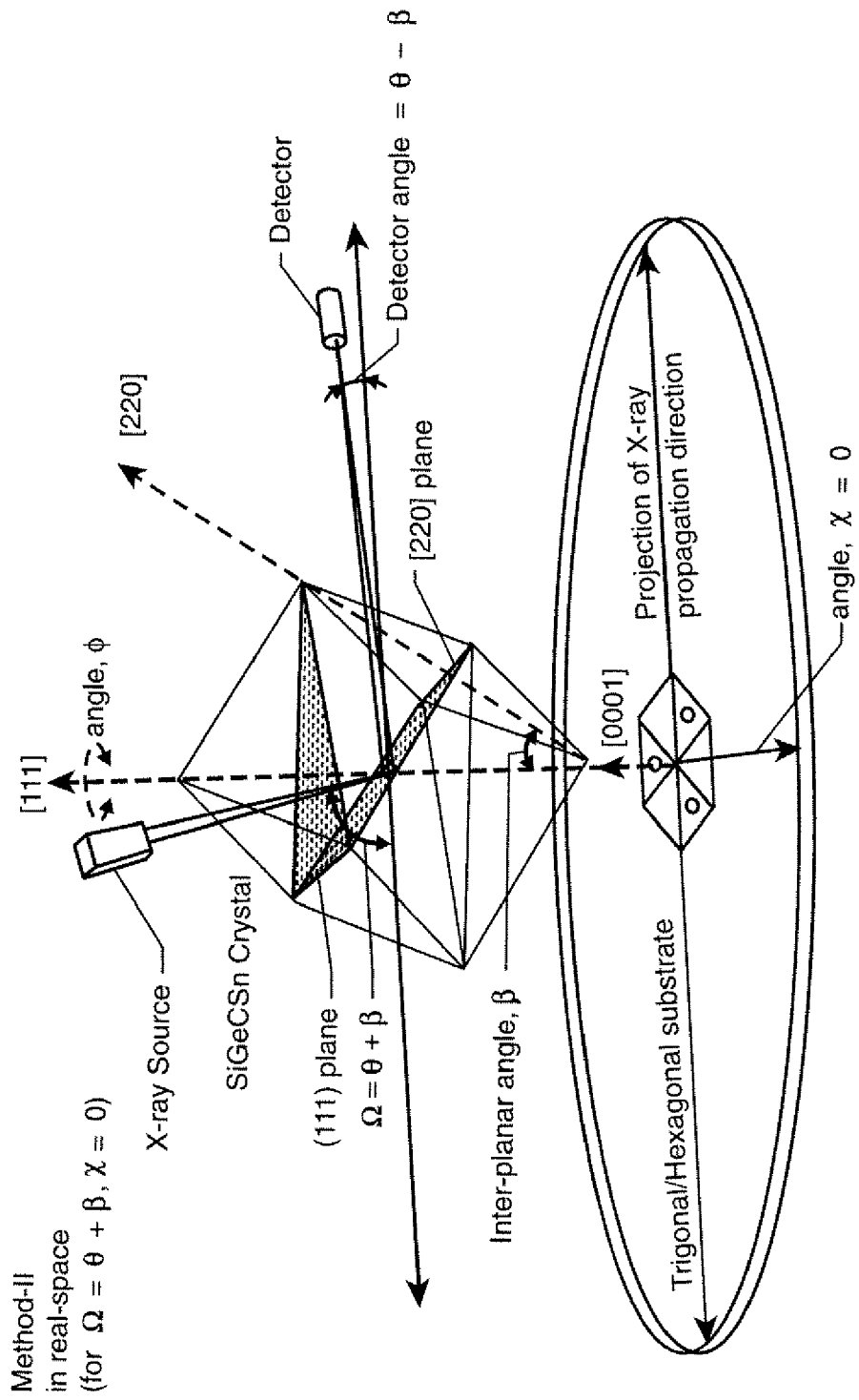
FIG. 11 is a schematic illustration showing the apparatus of X-ray diffraction method-2 of the related XRD disclosures.
Figure 12:
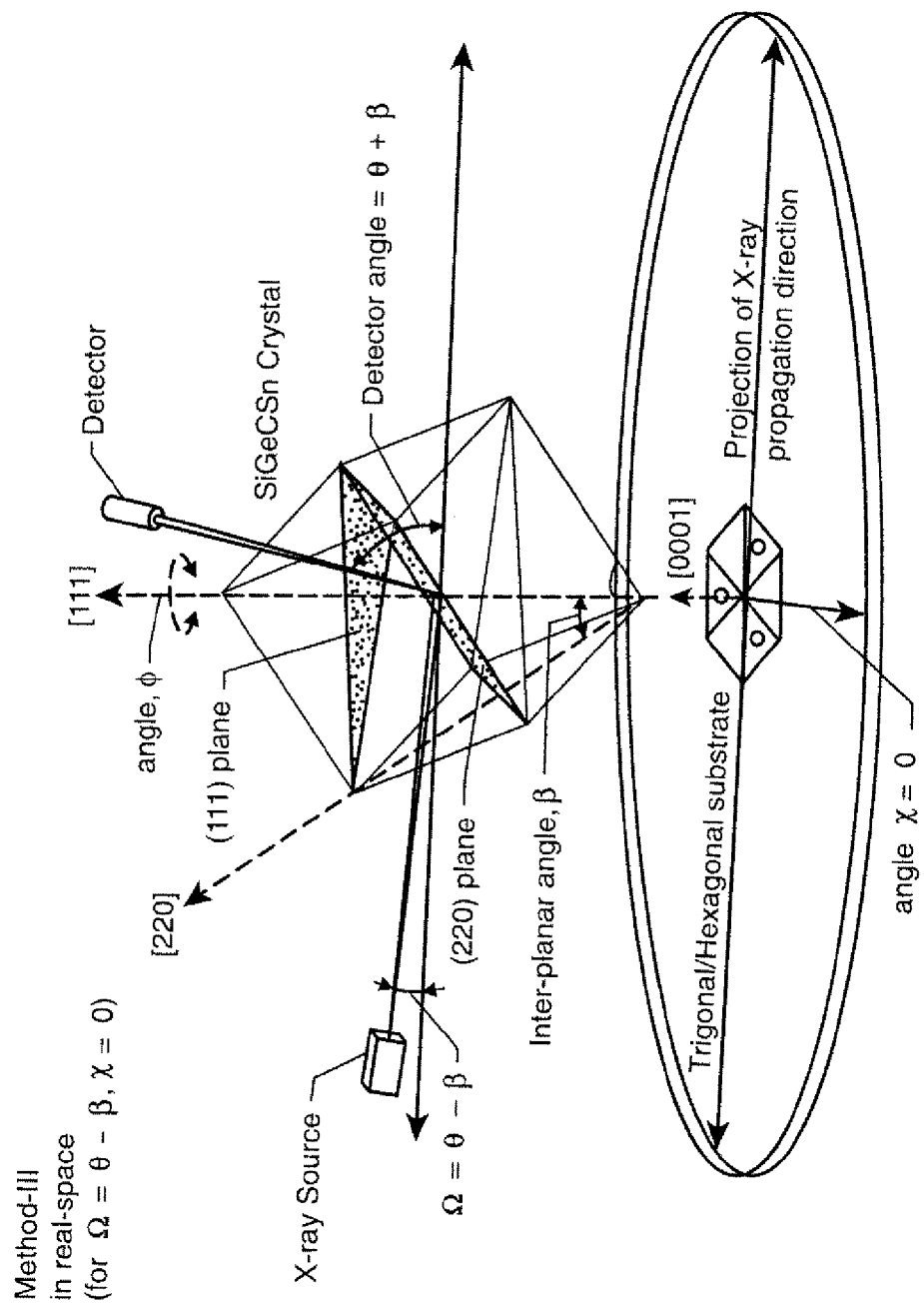
FIG. 12 is a schematic illustration showing the apparatus of X-ray diffraction method-3 of the related XRD disclosures.

FIGS. 10, 11, and 12 show the three detailed X-ray diffraction methods reported in the XRD disclosure "METHOD OF GENERATING X-RAY DIFFRACTION DATA FOR INTEGRAL DETECTION OF TWIN DEFECTS IN SUPER-HETERO-EPITAXIAL MATERIALS." By measuring three {220} X-ray diffraction peaks in Phi(φ)-scan, a single crystalline cubic material must show only three peaks which are apart from each other by 120°.

The techniques described in the XRD disclosures are not limited to group IV alloys. Cubic crystal includes group IV elements in diamond structure, group III-V and II-VI elements in zinc-blende structure as well as other elements in Body Centered Cubic (BCC) and Face Centered Cubic (FCC) structures. The above four lattice matching equations apply for all these materials. The X-ray diffraction methods of the XRD disclosures may be applied on these lattice matching conditions, on group IV, III-V, II-VI semiconductors, and rhombohedrally-lattice-matched FCC and BCC materials on various trigonal substrates.

(3) Grown Samples and Measured Data

As further detailed in the CRYSTAL GROWTH disclosure, a series of p-type and n-type SiGe alloy layers were grown on top of c-plane sapphire which has trigonal space symmetry, as shown in FIG. 13. The X-Ray Diffraction (XRD) analysis of some of the resulting samples is shown in the series of data in FIGS. 14-19.

Figure 14:
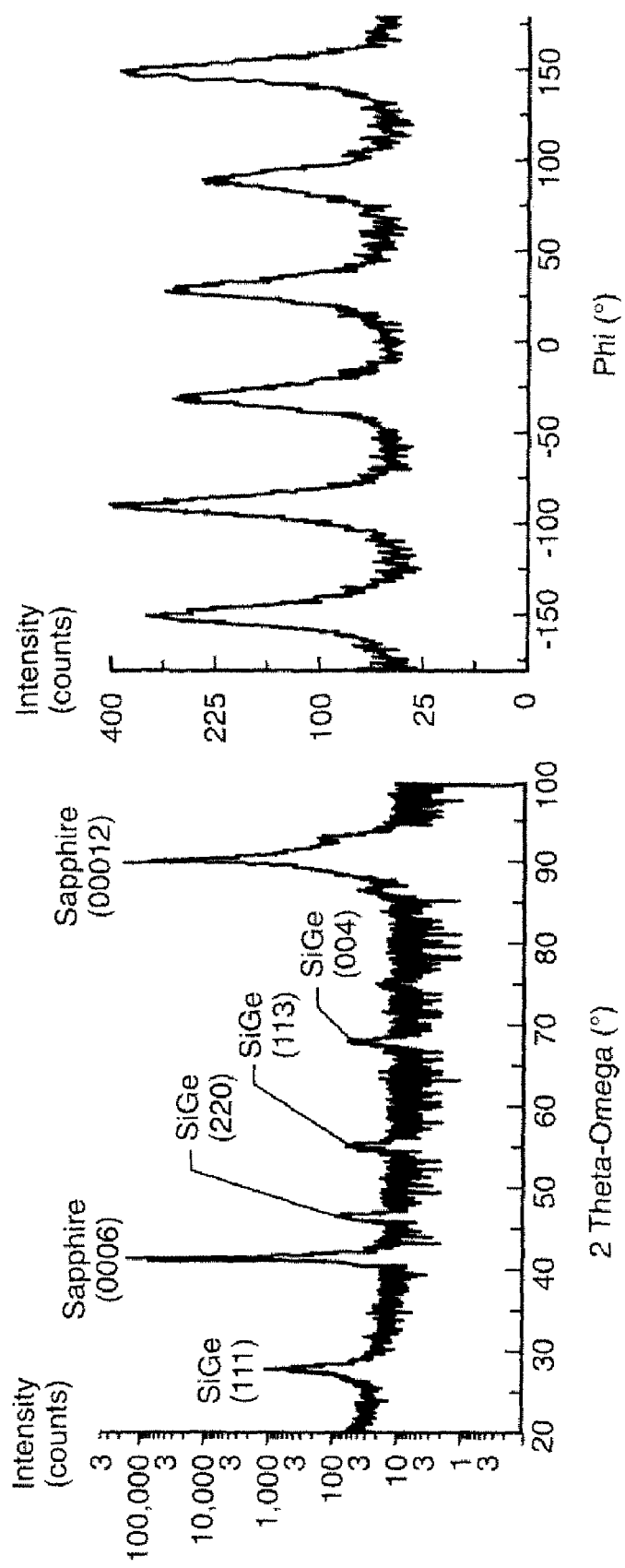
FIG. 14 contains graphs showing (Left) XRD normal scan of polycrystalline sample and (Right) Phi Scan of SiGe {220} peaks from the same sample.

A typical polycrystalline SiGe layer on c-sapphire shows multiple peaks in normal XRD scan data as shown in the left graph of FIG. 14. The SiGe {220} Phi Scan of such a sample often shows that {220} peaks are quite randomly distributed as shown in the right graph of FIG. 14.

Figure 15:
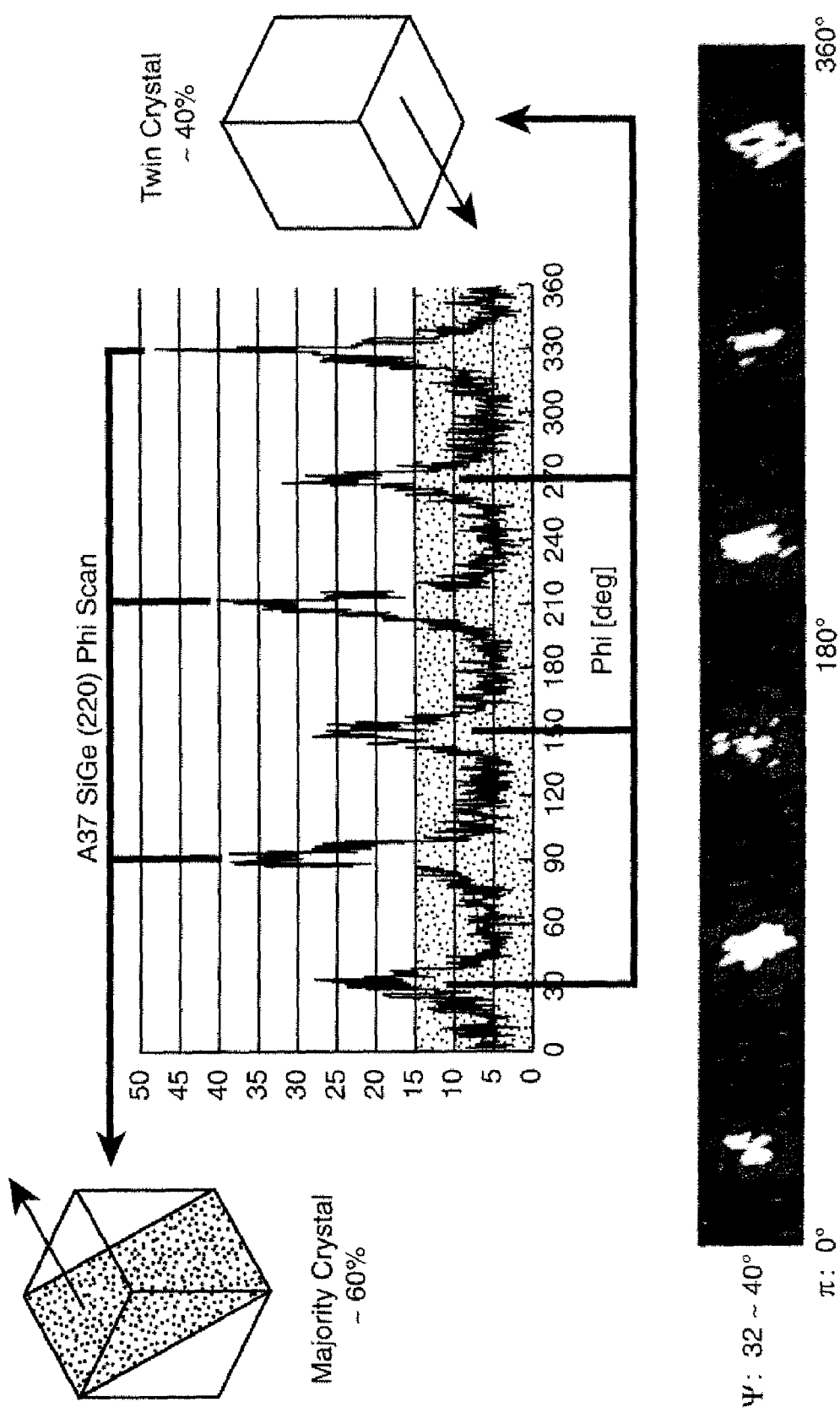
FIG. 15 shows analysis of SiGe {220} Phi Scan from improved sample, (above) Phi Scan of SiGe {220} peaks and (below) Intensity Plot of Phi-Psi Scan of SiGe {220} peaks.

On the other hand, the highly oriented samples in [111] direction on c-plane sapphire show a very strong SiGe (111) peak in the normal XRD scan, and they show a symmetry breaking in the Phi Scan of SiGe {220} peaks as shown in FIG. 15. About 60:40 ratio of symmetry breaking occurred in FIG. 15. The reason for this inequality was that there existed a difference in the formation energy of two diamond crystals which are rotated by 60°.

Figure 16B:
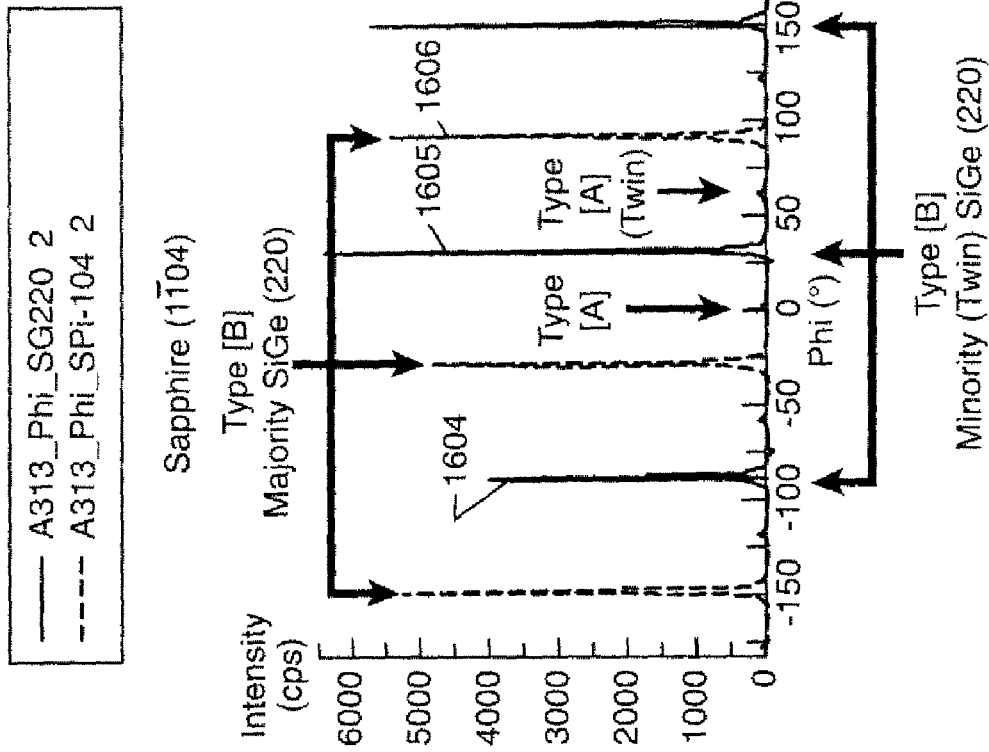
FIG. 16 contains plots showing Phi Scan of SiGe {220} and sapphire {1-104} peaks: (a) Sample #A37—whole SiGe in Type [B] alignment and (b) Sample #A313—mixture of type [B] and type [A] alignment.
Figure 16A:
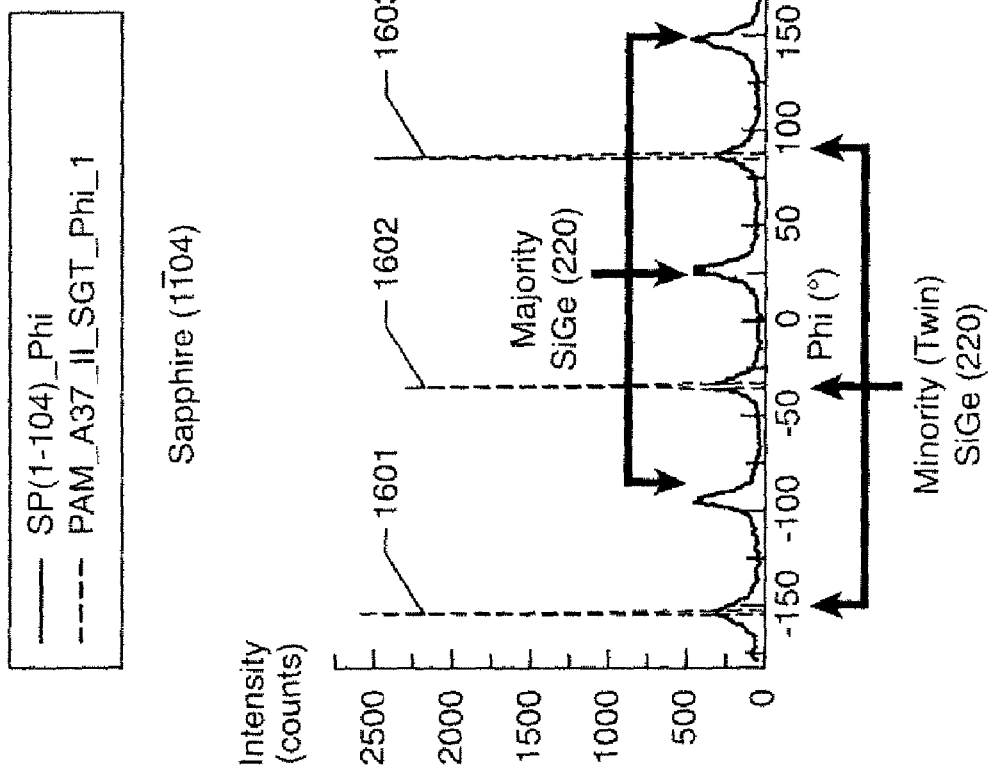

Phi-psi scan was also developed to compensate any sample-misalignment problem, as shown in the bottom graphic of FIG. 15. The XRD Phi Scan and Phi-psi scan of three-fold inclined planes around the <111> direction of cubic crystals is referred to as the "Twin Detection XRD Method". This method becomes clearer when the epitaxial layer peaks' phi angles are compared with XRD peaks from the substrate's inclined planes, such as sapphire {1-104} peaks, which are shown as lines 1601-1606 in FIG. 16. A mixture of Type [A] alignment and Type [B] alignment can also occur in some growth conditions, as shown in FIG. 16(*b*).

Figure 17:
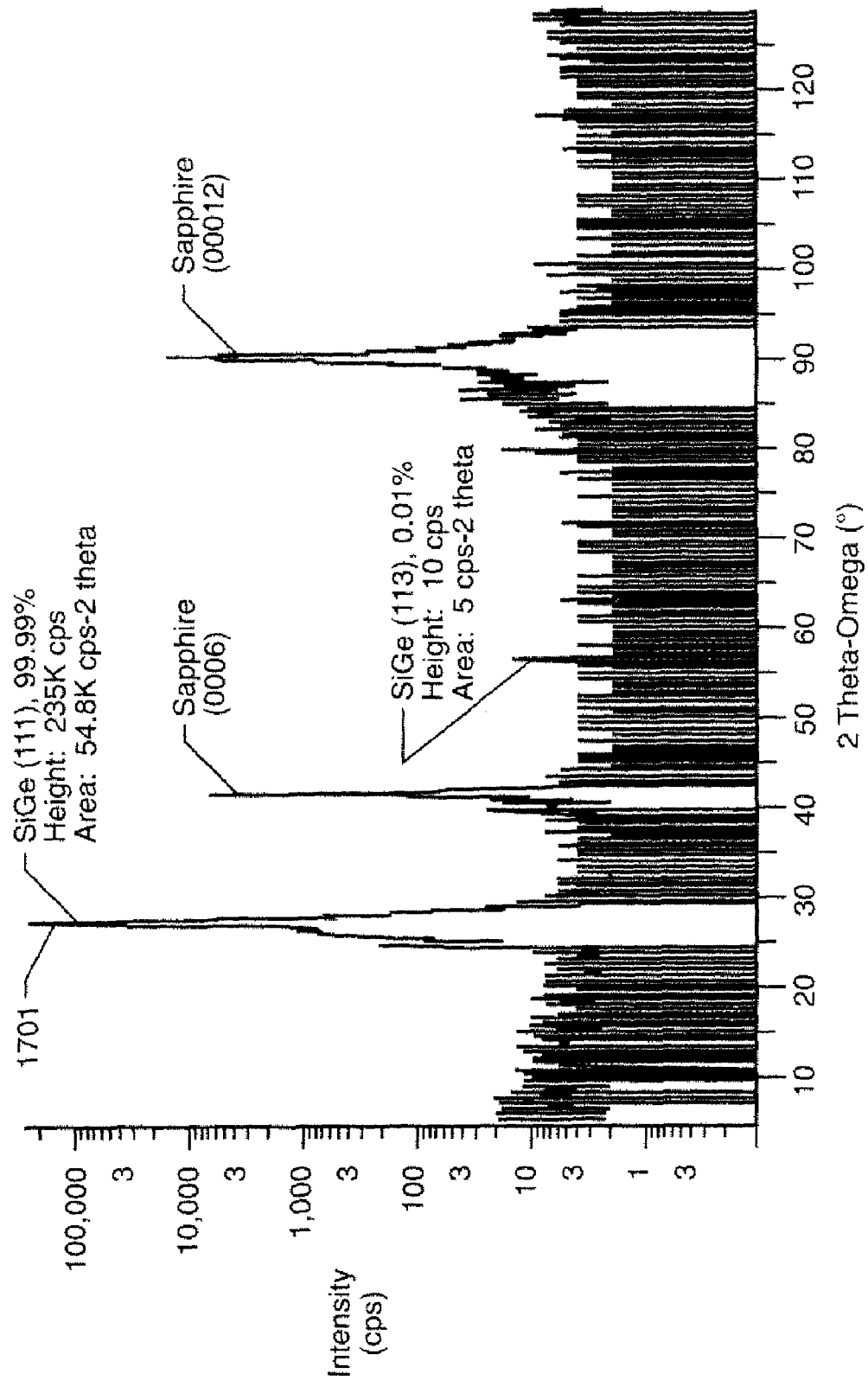
FIG. 17 is a plot showing an XRD normal scan of highly oriented (99.99% in [111] direction) SiGe Layer on c-plane sapphire.

The highly oriented SiGe layer on c-plane sapphire has an ultra strong (111) peak 1701 when it is compared with other peaks in XRD normal scan, as shown in FIG. 17. About 99.99% of SiGe layer is oriented in [111] direction in terms of peak height and peak area, compared with SiGe (113) peak.

Figure 18:
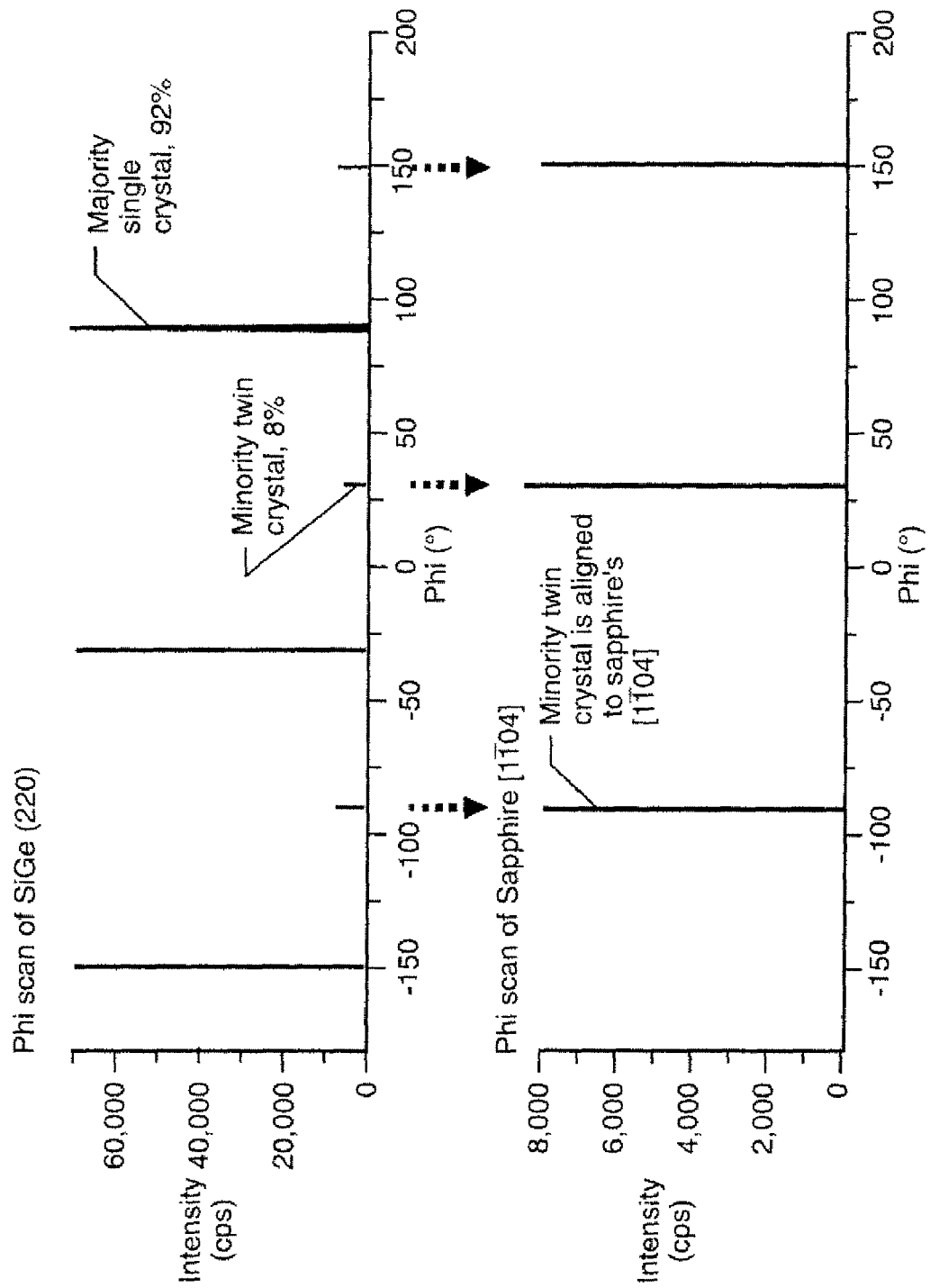
FIG. 18 illustrates plots showing Phi Scan of SiGe {220} peaks with a super symmetry breaking, in which the ratio of majority single crystal:minority twin crystal=92:8.

The Phi Scan of SiGe {220} peaks show that 92% of layer is the majority single crystal and 8% is the 60° rotated twin crystal on (111) plane as shown in FIG. 18. The super-symmetry breaking (92:8) shows the existence of a "golden" growth condition, which utilizes the difference of formation energy of two crystals on basal plane of trigonal substrate in trigonal space symmetry group.

Figure 19:
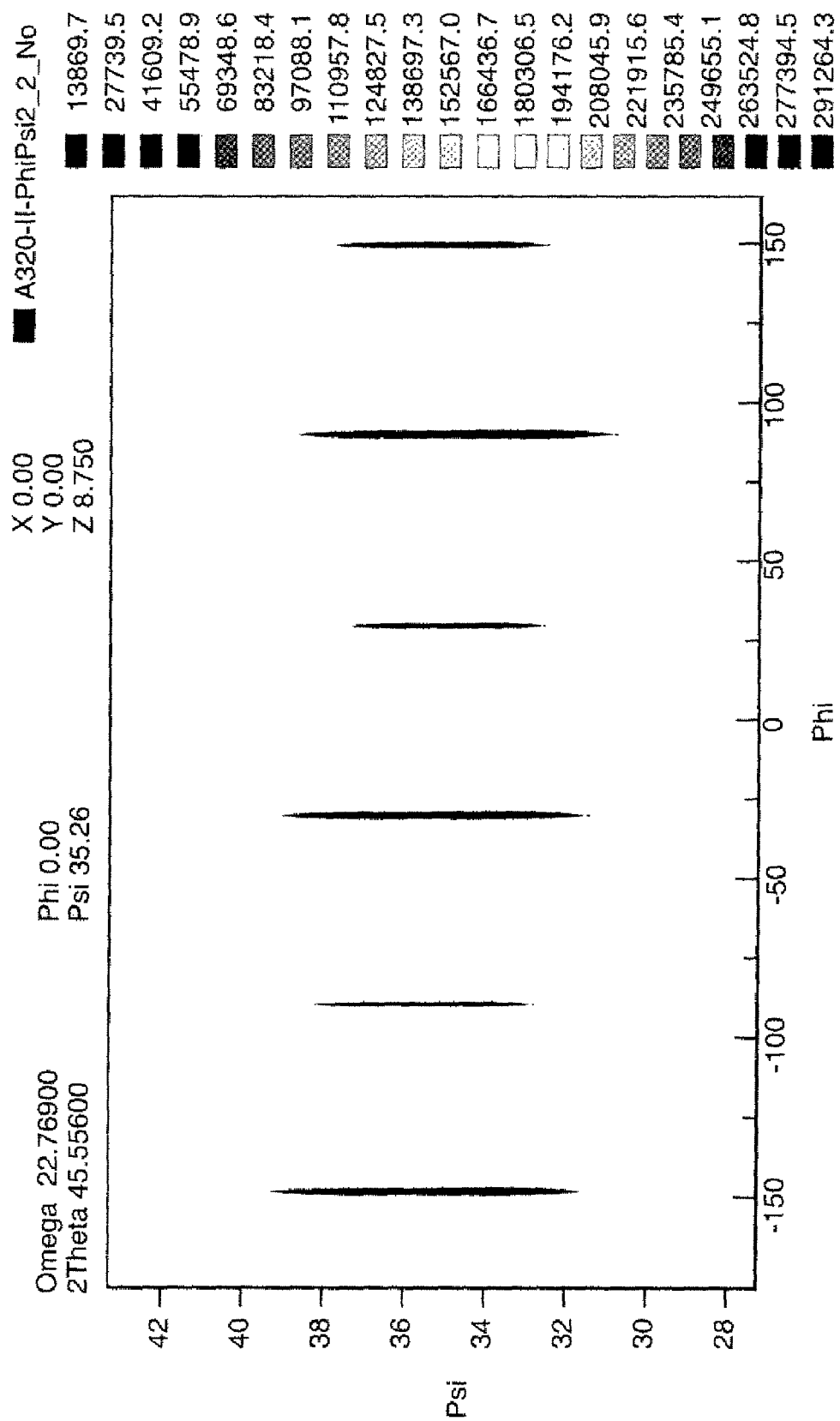
FIG. 19 is a plot of Phi-Psi scan of SiGe {220} peaks also showing a large symmetry breaking.

Phi-psi scan of the same sample also confirms the super symmetry breaking, as shown in FIG. 19.

From the above data, the stable majority single-crystalline SiGe crystal on c-plane sapphire forms the atomic alignment as shown in FIG. 20. Three small parallelograms 2001, 2002 and 2003 of SiGe crystal indicate three {100} cubic facet planes surrounding vertical <111> direction (out of the paper in this diagram.)

(4) Tri-Unity Relationship

The extraordinary symmetry breaking (92:89 of highly oriented (99.99% in [111] direction) SiGe layer on c-plane sapphire indicates that there exists a golden growth condition to grow single crystalline [111] oriented SiGe layer (Cubic) on c-plane sapphire (Trigonal Space Symmetry). Based on these observations, we conclude that there exists a fundamental inter-crystal-structure epitaxial relationship and we refer to it as "Tri-Unity" epitaxial relation because three different crystal structures, cubic (diamond, zinc-blende, FCC, BCC and so on), trigonal (space symmetry), and hexagonal (space symmetry, wurtzite and so on) crystals can be integrated in one continuous epitaxial structure. This relationship is drawn in FIG. 21, along with the corresponding validity of Twin Detection XRD Methods for each type of relation. For those relations for which the Twin Detection XRD Method is applicable, it can be used to monitor the epitaxial layers as a non-destructive evaluation tool. It can be used for quality control and selection of prime wafers. The Twin Detection XRD Method can also be used to verity structures and as a key tool in developing unprecedented crystal alloy systems.

Figure 21:
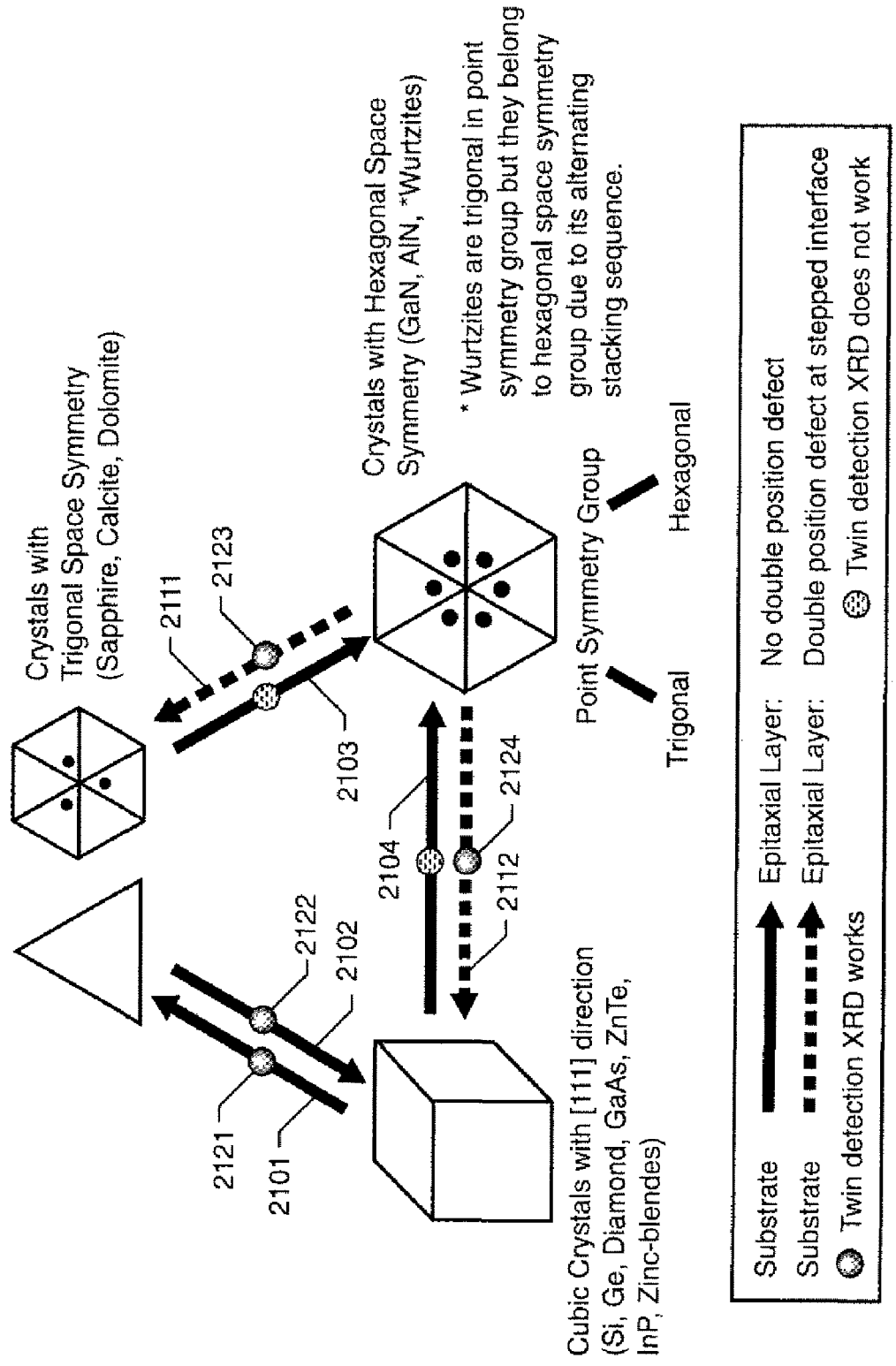
FIG. 21 is a graphic showing super-hetero-epitaxial relationships and validity of twin detection XRD methods for those relationships.

In the Tri-Unity diagram of FIG. 21, arrows are drawn from each underlying crystal structure such as substrate to an epitaxial crystal structure. All three crystal structures satisfy 120° rotational symmetry along cubic [111] or trigonal/hexagonal [0001] axes. However, double position defects can occur if the underlying crystal has hexagonal space symmetry including III-N wurtzite crystal structure, because it has additional 60° rotational space symmetry. The epitaxial growth with inevitable double position defect is drawn in dotted arrows 2111 and 2112. The epitaxial growth combinations marked with solid lines 2101, 2102, 2103, and 2104 can avoid double position defects that make twin crystals. The defect-free (no twin crystal) growth in solid line combinations occurs in certain narrow "golden" growth conditions by utilizing the difference in the formation energy (as explained at greater length in the CRYSTAL GROWTH disclosure).

As for the dotted epitaxial lines 2111 and 2112, in spite of the interfacial double position defect at the interface, a possibility that a single crystalline layer can be formed by internal stacking faults and domain expansion phenomena in which domain size becomes larger than a wafer size or a region of interest is not excluded. One example of such a domain expansion is the spinodal decomposition.

As for the diatomic and more complex cubic crystals, such as zinc-blendes (GaAs, AlP, and so on), atomic inversion defect such as Ga—As vs. As—Ga can occur since {111} planes are polarized planes. However, the inversion defects will not be considered here because they are more related with specific stacking sequence.

Figure 22:
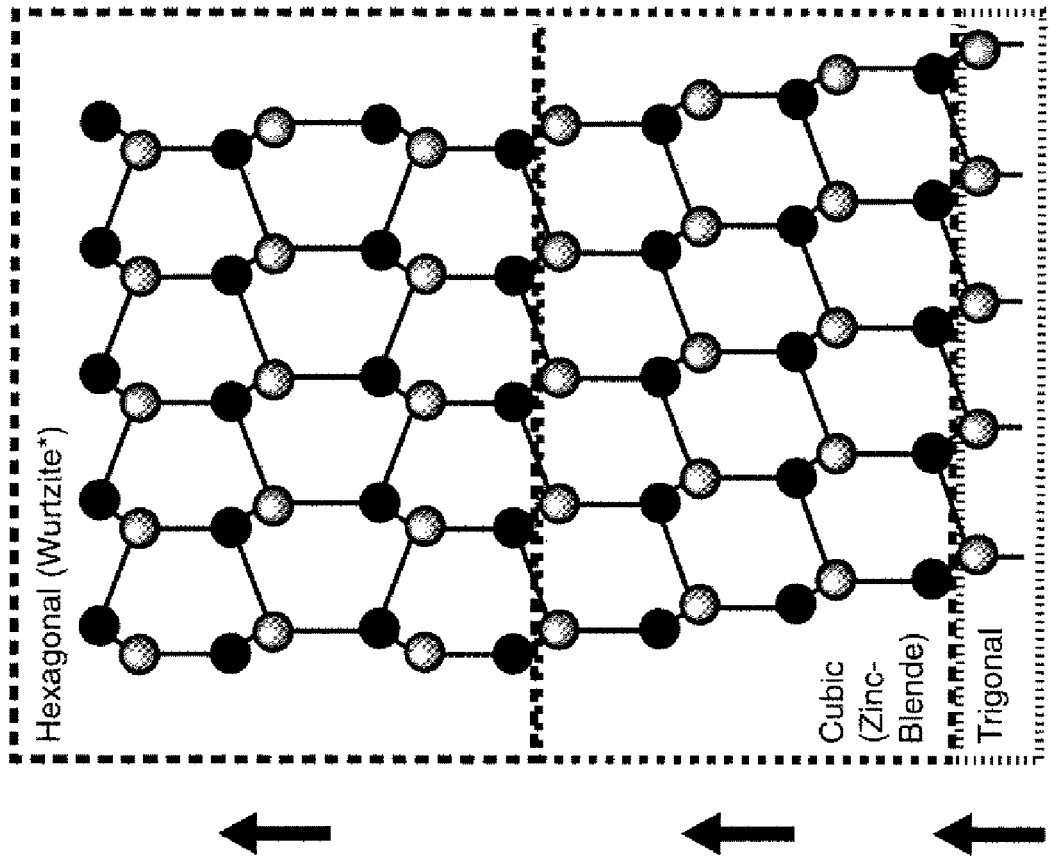
FIG. 22 is a schematic illustration showing an example of super-hetero-epitaxy with Tri-Unity relationship: trigonal [0001]→cubic (zinc-blende) [111]→hexagonal [0001].

FIG. 22 shows one example of rhombohedral super-hetero-epitaxy with a good Tri-Unity epitaxial relationship. Hexagonal wurtzite structure can repair double position defect by vertical strain of c/2 as shown by Sohn and Lilienthal-Weber et al. (Z. Liliental-Weber, H. Sohn, N. Newman, J. Washburn, Journal of Vacuum Science & Technology B 13 (4): 1578-1581 July-August 1995). Therefore, such a continuous epitaxial structure can be grown without propagating twin defects in a certain golden growth condition.

With the Tri-Unity epitaxial relation, our LATTICE MATCHING disclosure becomes a special case of [Trigonal (Space Symmetry)→Cubic] and [Hexagonal (Space Symmetry)→Cubic] in FIG. 21.

The twin detection XRD methods reported in the XRD disclosures apply to the various epitaxial relations that have circles 2121, 2122, 2123, and 2124 in FIG. 21.

Accordingly, application of twin detection XRD methods on the epitaxial systems shown in Table 1 is valid:

TABLE 1

Figure 23:
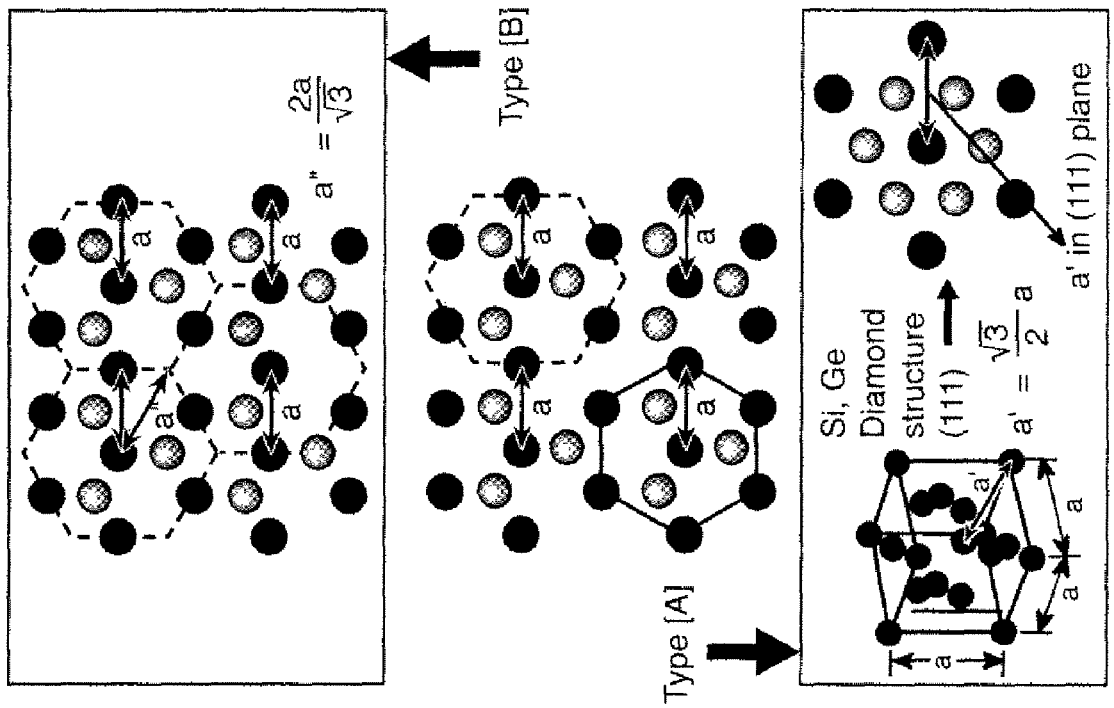
FIG. 23 shows schematic illustrations to be viewed in conjunction with Tables 3 and 4, showing transformed lattice constants (Å) of cubic semiconductor crystals and trigonal crystals.

Application of twin detection XRD methods on epitaxial systems (1) <111> Cubic Crystal Layer on {0001} Plane of Trigonal (Space Symmetry) Crystal Material Layer or Substrate
(2) <0001> Trigonal Crystal Layer on {111} Plane of Cubic Crystal Material Layer or Substrate
(3) <111> Cubic Crystal Layer on {0001} Plane of Hexagonal (Space Symmetry) Crystal Material Layer or Substrate
(4) <0001> Trigonal Crystal Layer on {111} Plane of Hexagonal (Space Symmetry) Crystal Material Layer or Substrate (5) New Bandgap Engineering for Rhombohedral Super-Hetero-Epitaxy The transformed lattice constants in Type [A], ⅔ of Type [A], Type [B], and ½ or Type [B] alignments are shown in Tables 2 and 3 below and FIG. 23.

TABLE 2

Transformed Lattice Constants of Cubic Semiconductor Materials

| Group | Material | A | C | Type A's a' | Eg(eV) |
| --- | --- | --- | --- | --- | --- |
| III-V | GaAs | 5.65 | 5.65 | 4.90 | 1.42 |
|  | AlAs | 5.66 | 5.66 | 4.90 | 2.15 |
|  | InAs | 6.06 | 6.06 | 5.25 | 0.35 |
|  | GaP | 5.45 | 5.45 | 4.72 | 2.27 |
|  | InP | 5.87 | 5.87 | 5.08 | 1.34 |
|  | InSb | 6.48 | 6.48 | 5.61 | 0.17 |
|  | AlP | 5.46 | 5.46 | 4.73 | 2.45 |
| IV | Si | 5.43 | 5.43 | 4.70 | 1.12 |
|  | Ge | 5.66 | 5.66 | 4.90 | 0.66 |
|  | C | 3.57 | 3.57 | 3.09 | 5.50 |
| II-VI | ZnS | 5.42 | 5.42 | 4.69 | 3.60 |
|  | ZnSe | 5.70 | 5.70 | 4.94 | 2.60 |
|  | CdSe | 6.05 | 6.05 | 5.24 | 1.60 |

TABLE 3

Transformed Lattice Constants of Trigonal Crystals

| Substrates | A | C | Type [B]'s a" |
| --- | --- | --- | --- |
| Sapphire | 4.76 | 12.99 | 5.49 |
| Calcite | 4.99 | 17.06 | 5.76 |
| LaF3 | 7.19 | 7.37 | 8.30 |
| Langasite (La3Ga5SiO14) | 8.18 | 5.10 | 9.44 |

Because rhombohedral super-hetero-epitaxy uses transformed lattice constant, the bandgap engineering diagrams of bandgap energy vs. lattice constant have to be redrawn. The positions of many diamond group IV and zinc-blende III-V and II-VI semiconductor materials in Type [A] and ⅔ of Type [A] alignment are plotted in FIG. 24 and include a few new possible trigonal (space symmetry) crystal substrates' lines for lattice matching conditions. (As explained in the LATTICE MATCHING disclosure, the detailed alloy lines in these diagrams may be further refined inside group IV, group III-V, group II-VI, and group III-nitride areas by taking into consideration higher order parameters, such as Bowing parameters and direct-to-indirect bandgap changes.)

Figure 25:
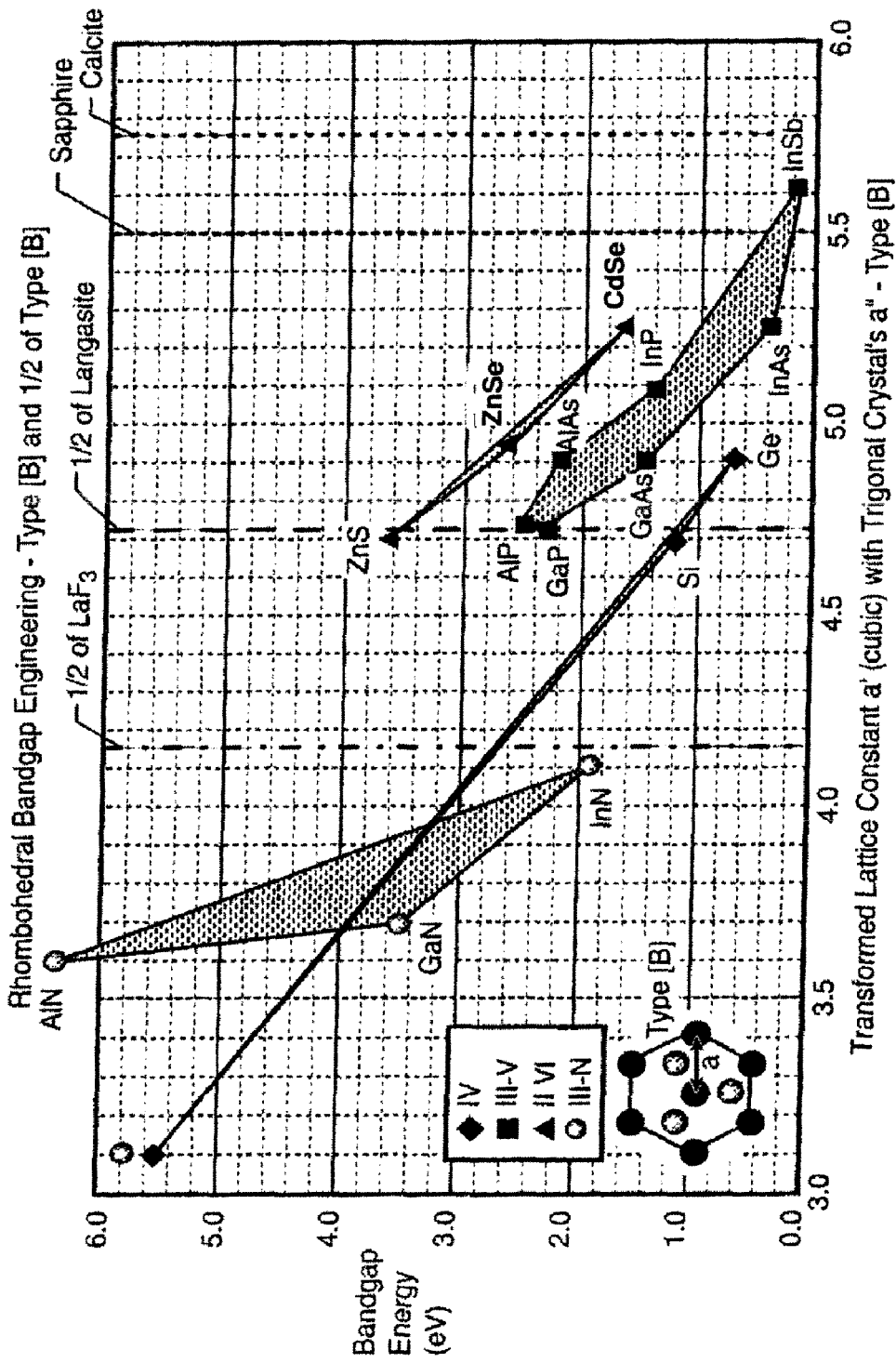
FIG. 25 is a graph showing bandgap energy vs. transformed lattice constant (Å) for super-hetero-epitaxy in Type [B] Alignment.

Similarly, the same type of bandgap engineering diagrams for Type [B] and ½ of Type [B] alignment are shown in FIG. 25.

The most common atomic alignment at interface is a mixture of Type [A] and Type [B], including the ⅔ and ½ fractional variants of these alignments. This frequent common mixed alignment is plotted in FIG. 26. Notice that the transformed lattice constant is different from cubic lattice constant. The well-known lattice mismatch of 13.7% between GaN and sapphire can be easily shown in this diagram.

Figure 24:
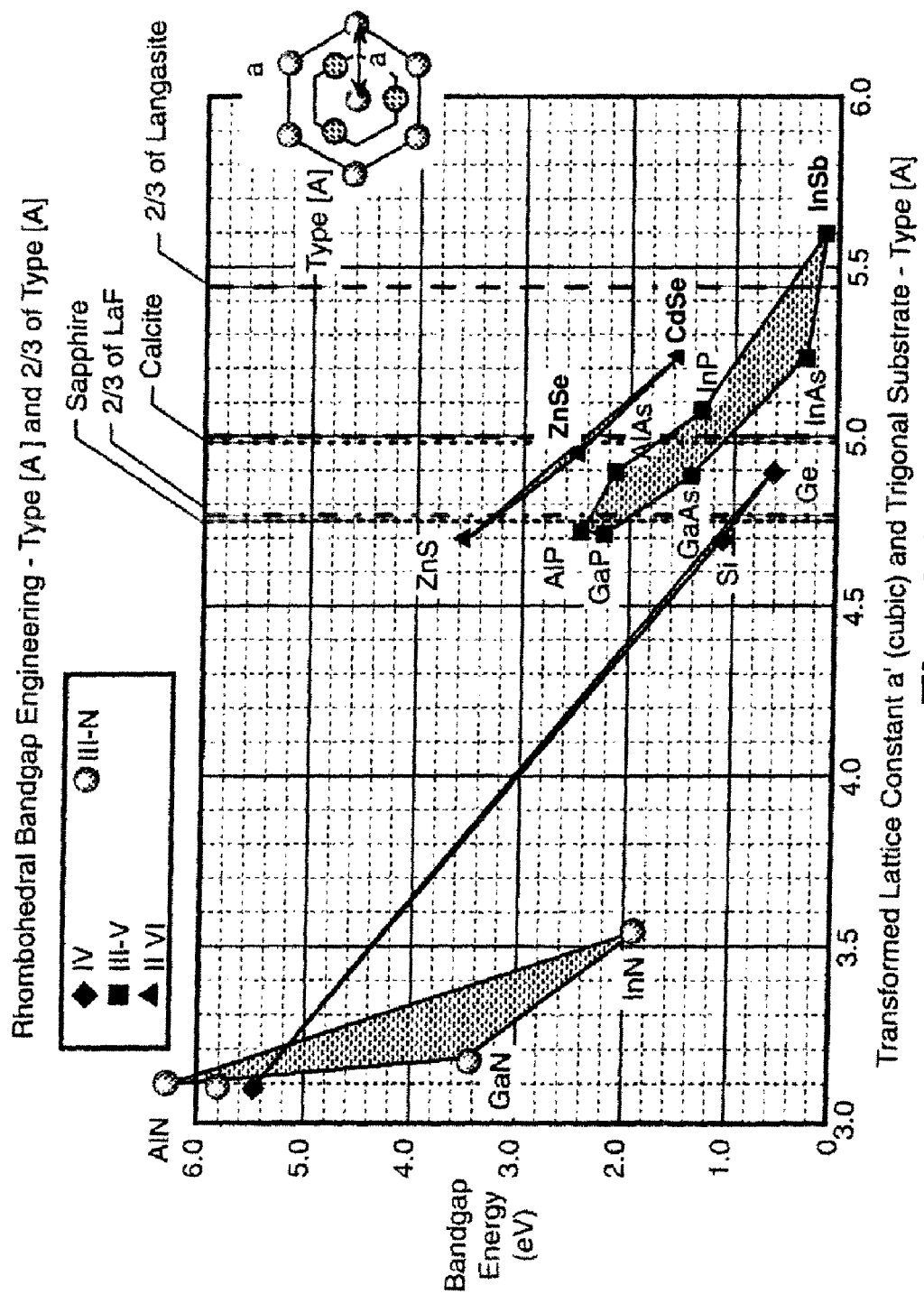
FIG. 24 is a graph showing bandgap energy vs. transformed lattice constant (Å) for super-hetero-epitaxy in Type [A] Alignment.
Figure 26:
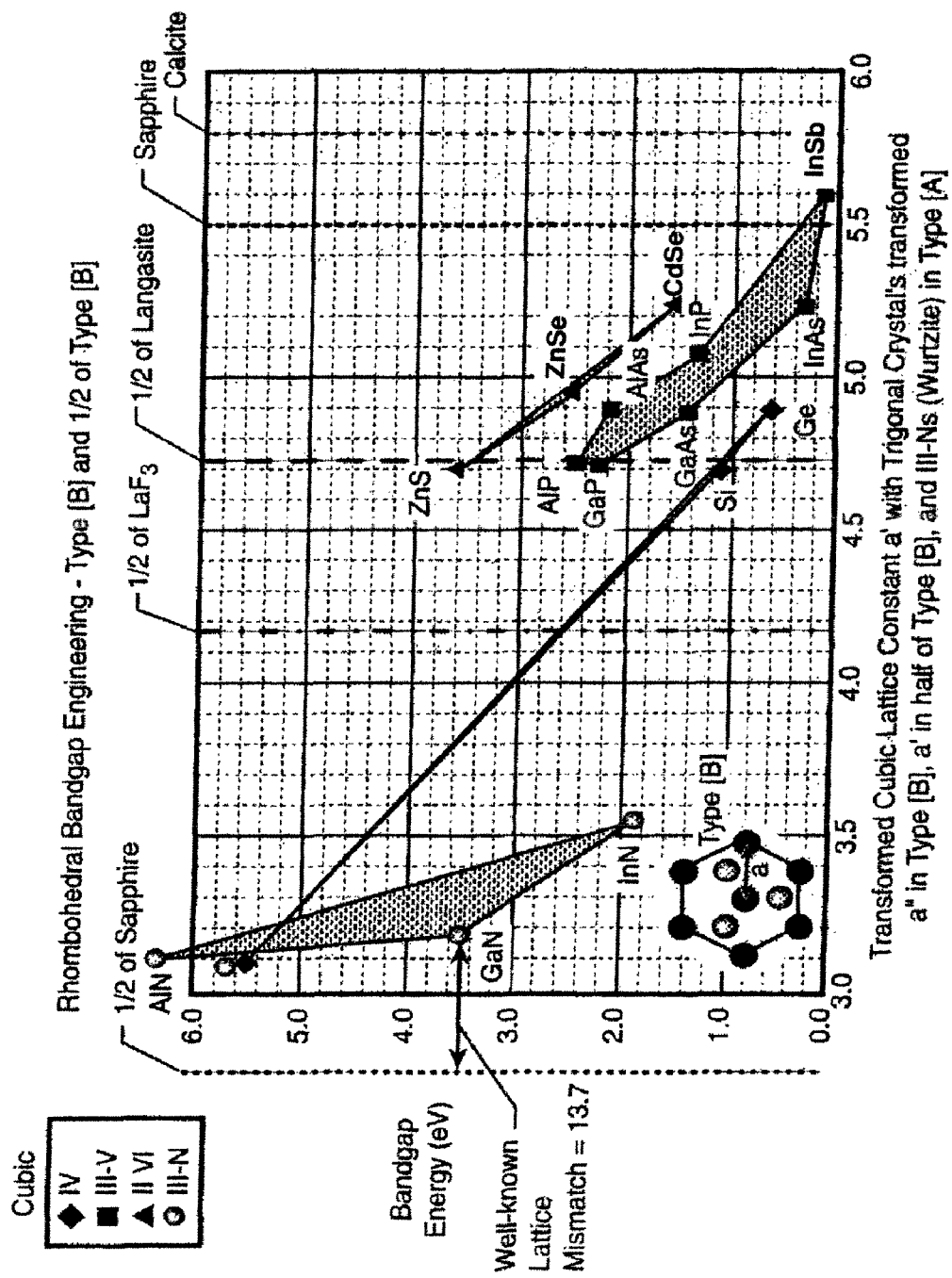
FIG. 26 is a graph showing bandgap energy vs. transformed lattice constant (Å) for super-hetero-epitaxy in mixed configuration (trigonal↔cubic: Type [B], trigonal↔hexagonal (wurtzite): Type [B], cubic↔hexagonal (wurtzite): Type [A]).

Unlike the previous bandgap engineering diagrams in FIG. 1, the rhombohedral super-hetero-epitaxy bandgap engineering diagrams in FIGS. 24, 25 and 26 predict unprecedented integrated alloys of different crystal structures in one continuous epitaxial structure.

These new bandgap engineering diagrams cover only a subset of possibilities and can be refined with more precise alley lines and expanded by adding more substrates. Nevertheless, it ifs certain that other useful alloys can be formulated by the methods described above and that these bandgap engineering diagrams can serve to support the entire global semiconductor industry as a roadmap for unprecedented super-hetero alloy material systems.

Some of the new materials made possible by the methods described above include the materials listed in Table 4.

TABLE 4

Application of New Bandgap Engineering to <111> Oriented Rhombohedrally Lattice-Matched Semiconductor Alloys
New <111> Oriented Rhombohedrally Lattice Matched Semiconductor Alloys (1) Group IV alloys (Si, Ge, C, and Sn) on c-plane LaF3: in half of Type [B] alignment
(2) Group IV alloys (Si, Ge, C, and Sn) on c-plane Langasite: in half of Type [B] alignment
(3) Group III-V alloys on c-plane Langasite: in half of Type [B] alignment
(4) Group II-VI alloys on c-plane Langasite: in half of Type [B] alignment
(5) Group III-V alloys on c-plane Sapphire: in Type [B] alignment Moreover, to the extent that strained InN, InGaN, and AlInN alloys on c-plane $LaF_3$ substrate can form ⅔ of Type [A] alignment, these could also give low lattice mismatch as shown in FIG. 24.

Thus, it is apparent that the methods and materials described in the present disclosure satisfy the objects of the invention set forth above. In particular, the present invention provides a rhombohedral super-hetero-epitaxy, an unprecedented hybrid bandgap engineering diagram, and mathematically-supported new lattice-matching models for deriving transformed lattice constants. The bandgap engineering diagrams summarize individual material-research efforts including novel material development, and also serve and as a long-term roadmap for future material development in accordance with the methods described herein. The invention also uses concurrently filed twin detection XRD methods and the Tri-Unity relationship diagram herein to assist with the rhombohedral super-hetero-epitaxy developments.

The present invention is further discussed in Y. Park, G. C. King, S. H. Choi, Rhombohedral epitaxy of cubic SiGe on trigonal c-plane sapphire, Journal of Crystal Growth 310 (2008) 2724-2731, herein incorporated by reference in its entirety.

Although the present invention has been described in detail, it should be understood that various changes, substitutions, and alterations may be readily ascertainable by those skilled in the art and may be made herein without departing from the spirit and scope of the present invention as defined by the following claims.

What is claimed as new and desired to be secured by Letters Patent of the United States is:

1. A method for quality control and selection of prime wafers in a rhombohedral, super-hetero epitaxial semiconductor material of a continuous epitaxial structure, said material comprising a substrate having a first crystal structure, and at least one epitaxial layer having a second crystal structure that differs from said first crystal structure, said method comprising
   a) using X-ray diffraction in which the combination of Omega (goniometer angle) and Chi (angle of [111] vector relative to the X-ray diffraction reference orientation) parameters, as a function of Theta (Bragg angle) and Beta (interplanar angle of alloy's {111} plane and selected non-perpendicular plane) are selected from the group consisting of (a) Chi=Beta, Omega=Theta; (b) Omega=Theta+Beta, Chi=0; and (c) Omega=Theta-Beta, Chi=0, in order to determine double position defects;
   b) wherein said X-ray diffraction method is applied where the correspondence of said first and second crystal structures are within the group consisting of (i)cubic on trigonal, (ii) trigonal on cubic, (iii) hexagonal on cubic, and (iv) hexagonal on trigonal (wherein trigonal and hexagonal refers to space, symmetry).

2. The method of claim 1 applied to super-hetero epitaxial, semiconductor material selected from the group consisting of:
   a) <111> cubic crystal layer on {0001} plane of trigonal crystal material layer or substrate;
   b) <0001> trigonal crystal layer on {111} plane of cubic crystal material layer or substrate;
   c) <111> cubic crystal layer on {0001} plane of hexagonal crystal material layer or substrate; and
   d) <0001> trigonal crystal layer on {111} plane of hexagonal crystal material layer or substrate.

3. A method for making a rhombohedral, super-hetero epitaxial semiconductor material of a continuous epitaxial structure having a selected bandgap energy comprising depositing on a substrate having a first crystal structure at least one epitaxial layer having a crystal structure that differs from said first crystal structure, said crystal structures each being from among the group consisting of cubic, trigonal (space symmetry) and hexagonal (space symmetry) wherein the first crystal structure and the crystal structure of at least one epitaxial layer are selected to have sufficiently similar transformed lattice constants to form a rhombohedral interface and the crystal structure of at least one epitaxial layer is selected to provide the selected bandgap energy, and wherein the correspondence of said first and second crystal structures are within the group consisting of (a) cubic on trigonal, (b) trigonal on cubic, (c) hexagonal on cubic, and (d) hexagonal on trigonal, further comprising performing quality control and selection of prime wafers by using X-ray diffraction in order to determine twin defects, and in which, for such X-ray diffraction, the combination of Omega (goniometer angle) and Chi (angle of {111} vector relative to the X-ray diffraction reference orientation) parameters, as a function of Theta (Bragg angle) and Beta (interplanar angle of said alloy's {111} plane and selected non-perpendicular plane) are selected from the group consisting of:
   i) Chi=Beta, Omega=Theta;
   ii) Omega=Theta+Beta, Chi=0; and
   iii) Omega=Theta-Beta, Chi=0.

* * * * *